(12) United States Patent
Nakatsugawa

(10) Patent No.: US 9,695,396 B2
(45) Date of Patent: Jul. 4, 2017

(54) REGENERATED TISSUE COMPRISING A STRATIFIED STRUCTURE OF EPITHELIAL CELLS

(71) Applicant: JAPAN SCIENCE AND TECHNOLOGY CORPORATION, Saitama (JP)

(72) Inventor: Shigekazu Nakatsugawa, Aichi (JP)

(73) Assignee: SHIGEKAZU NAKATSUGAWA, Nagoya-Shi (JP)

( * ) Notice: Subject to any disclaimer, the term of this patent is extended or adjusted under 35 U.S.C. 154(b) by 0 days.

(21) Appl. No.: 14/058,885

(22) Filed: Oct. 21, 2013

(65) Prior Publication Data
US 2014/0147831 A1 May 29, 2014

Related U.S. Application Data

(62) Division of application No. 10/492,688, filed as application No. PCT/JP02/10674 on Oct. 15, 2002, now Pat. No. 8,592,176.

(30) Foreign Application Priority Data

Oct. 15, 2001 (JP) ................. 2001-317502

(51) Int. Cl.
| | |
|---|---|
| C12N 5/071 | (2010.01) |
| A61L 27/38 | (2006.01) |
| A61L 27/36 | (2006.01) |
| A61K 35/12 | (2015.01) |

(52) U.S. Cl.
CPC ........ *C12N 5/0625* (2013.01); *A61L 27/3604* (2013.01); *A61L 27/3813* (2013.01); *C12N 5/0697* (2013.01); *A61K 35/12* (2013.01); *C12N 2502/088* (2013.01); *C12N 2502/095* (2013.01); *C12N 2502/246* (2013.01); *C12N 2502/256* (2013.01); *C12N 2502/28* (2013.01); *C12N 2502/30* (2013.01); *C12N 2503/00* (2013.01); *C12N 2503/04* (2013.01)

(58) Field of Classification Search
CPC ............ C12N 5/0697; C12N 2506/08; C12N 5/0631–5/0633; C12N 5/067–5/0689; C12N 5/069; C12N 5/0656
See application file for complete search history.

(56) References Cited

U.S. PATENT DOCUMENTS

| | | | |
|---|---|---|---|
| 4,016,036 | A | 4/1977 | Green et al. |
| 4,914,032 | A | 4/1990 | Kuri-Harcuch et al. |
| 5,866,414 | A | 2/1999 | Badylak et al. |
| 6,022,743 | A | 2/2000 | Naughton et al. |
| 6,730,513 | B1 | 5/2004 | Hunziker et al. |

FOREIGN PATENT DOCUMENTS

| | | |
|---|---|---|
| JP | 7-040931 | 5/1995 |
| WO | 00/29553 | 5/2000 |

OTHER PUBLICATIONS

Cells, Tissues and Membranes. Printed from http:///www.web-books.com/eLibrary/Medicine/Physiology/Cells/Cells.htm, as pp. 1/4-4/4 on Jul. 2, 2015.*
Tosh et al. How cells change their phenotype. Nature Reviews: Molecular Cell Biology, vol. 3, pp. 187-194, Mar. 2002.*
Liu et al. Transdifferentiation—Fact or Artifact. Journal of Cellular Biochemistry, vol. 88, pp. 29-40, 2003.*
Cotgreave, A. Session 3: Stress response. Toxicology in Vitro, vol. 12, pp. 569-573, 1998.*
Brannen et al. In vitro differentiation of multipotent human neural progenitors in serum-free medium. NeuroReport, vol. 11, No. 5, pp. 1123-1128, Apr. 2000.*
Hata et al. The characteristics of cultured mucosal sheet as a material for grafting; Comparison with cultured epidermal sheet. Annals of Plastic Surgery, vol. 34, No. 5, pp. 530-538, May 1995.*
Limat et al. Post-mitotic human dermal fibroblasts efficiently support the growth of human follicular keratinocytes. Journal of Investigative Dermatology, vol. 92, No. 5, pp. 758-762, May 1989.*
Vondracek et al. "Assessment of Keratin Expression and Xenobiotic Metabolism in Cultured Normal and Transformed Human Oral Keratinocytes." in Animal Cell Technology: From Target to Market (Proceedings of the 17th ESACT Meeting Tylösand, Sweden, Jun. 10-14, 2001, Lindner-Olsson, E., Chatzissavidou, N., Lüllau, E. (Eds.), pp. 143-147, 2001.*
Hansson et al. Expression of keratins in normal, immortalized and malignant oral epithelial in organotypic culture. Oral Oncology, vol. 37, pp. 419-430, Jul. 2001.*
John M. Shannon et al., "Functional Differentiation of Alveolar Type II Epithelial Cells in vitro: Effects of Cell Shape, Cell-matrix Interactions and Cell-Cell Interactions", Biochimica et Biophysica Acta, 1987, vol. 931, pp. 143-156.
Takahashi et al.; "Formation of micro-liver by intestine epithelial HGF in primary culture"; Naturwissenschaften, vol. 77, pp. 330-332, 1990.
Machine translation of JP7040931 B, printed on Oct. 12, 2009 as pp. 1/11 to 11/11.
Ries et al.; "Elevated expression of hormone-regulated rat hepatocyte functions in a new serum-free hepatocyte-stromal cell coculture model"; In Vitro Cell. Dev. Bioi.—Animal, vol. 36, No. 8, pp. 502-512, Sep. 2000.

(Continued)

*Primary Examiner* — Jennifer Dunston
(74) *Attorney, Agent, or Firm* — Wenderoth, Lind & Ponack, L.L.P.

(57) ABSTRACT

A normal regenerated tissue is formed by exposing to radiation a connective tissue or a supporting tissue originating in an organ to thereby form a feeder layer and then transplanting epithelial cells thereon to form a stratified structure. By conveniently and surely providing regenerated tissue by the 3-dimensional culture with the use of a human-origin normal tissue as a base, it is possible to construct systems for assessing effects and side effects of chemicals such as drugs or assessing sensitivities thereof with the use of regenerated tissues as models of corresponding tissues respectively.

7 Claims, 54 Drawing Sheets

(56) References Cited

OTHER PUBLICATIONS

LeCluyse et al.; "Strategies for restoration and maintenance of normal hepatic structure and function in long-term cultures of rat hepatocytes"; Advanced Drug Delivery Reviews, vol. 22, pp. 133-186, 1996.

Aaltonen et al.; "A novel method to culture laryngeal human papillomavirus-positive epithelial cells produces papilloma-type cytology on collagen rafts"; European Journal of Cancer, vol. 34, No. 7, pp. 1111-1116, 1998.

Wheater et al.; "Wheater's Functional Histology: A Text and Colour Atlas"; New York: Churchill Livingstone, Inc., 1993, p. 61.

Smola et al.; "Mutual induction of growth factor gene expression by epidermal-dermal cell interaction"; The Journal of Cell Biology, vol. 122, No. 2, pp. 417-429, Jul. 1993.

\* cited by examiner

Fig. 14
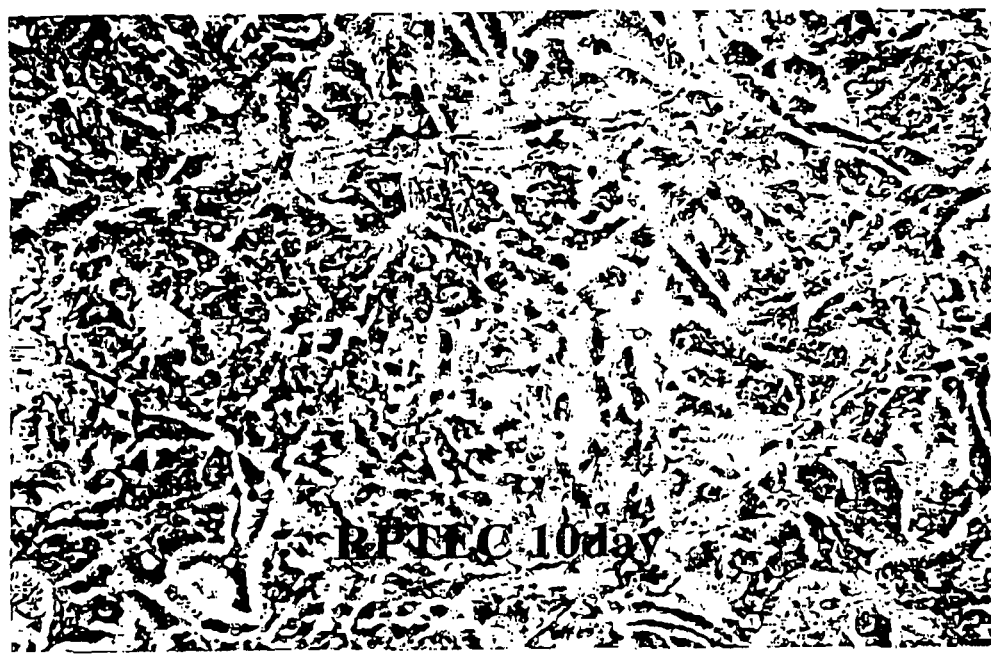
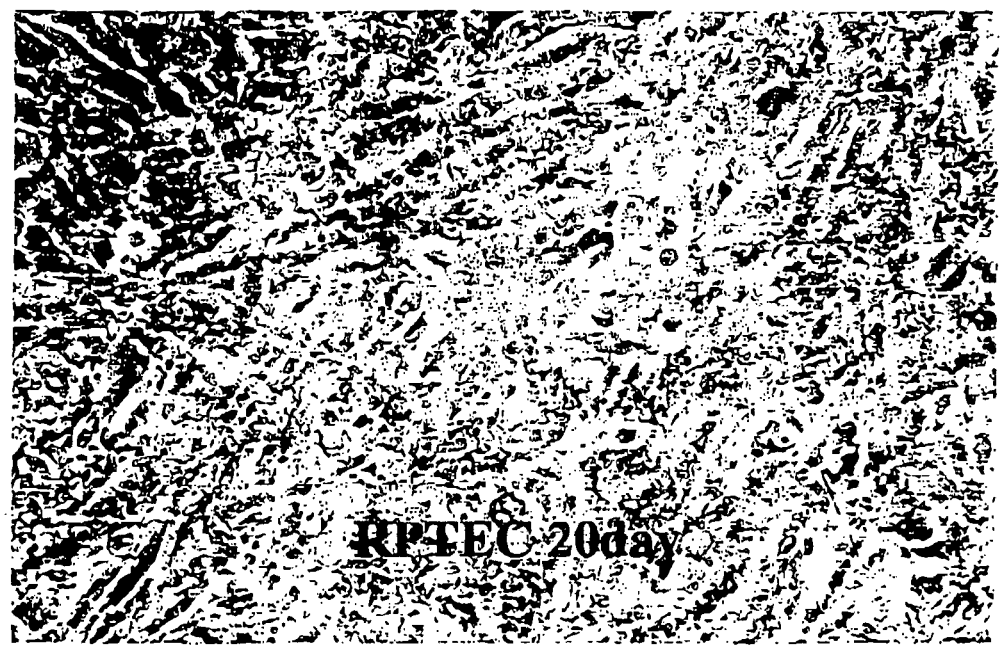

Fig. 15
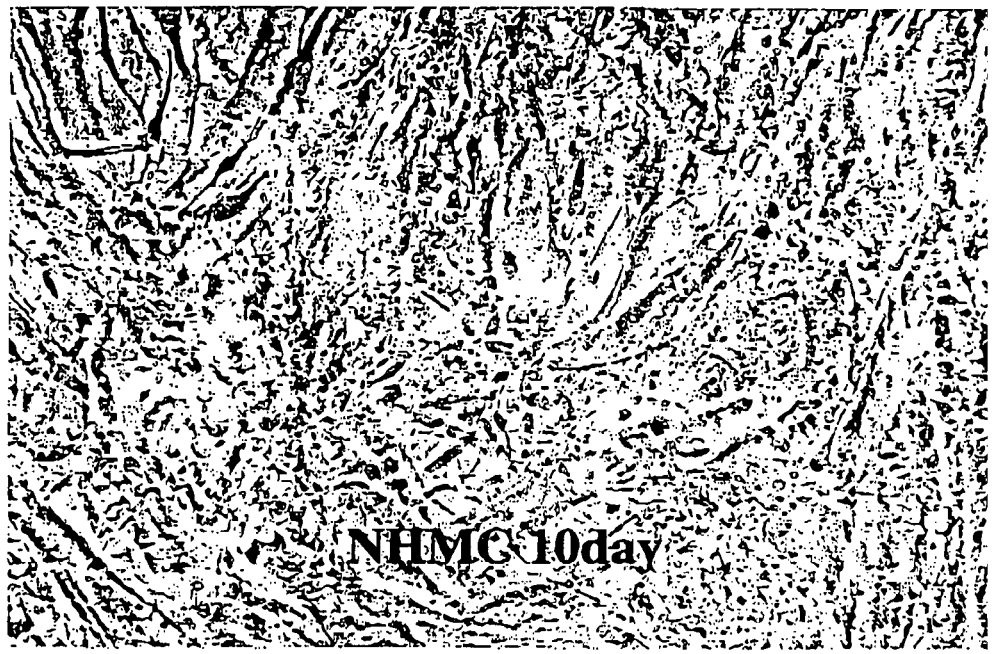
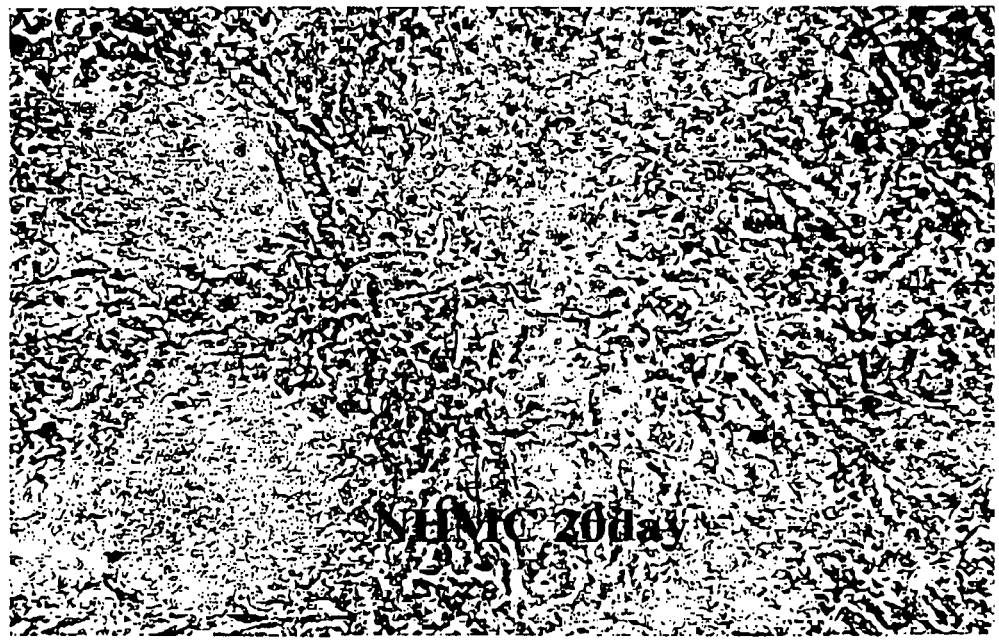

Fig. 1 6
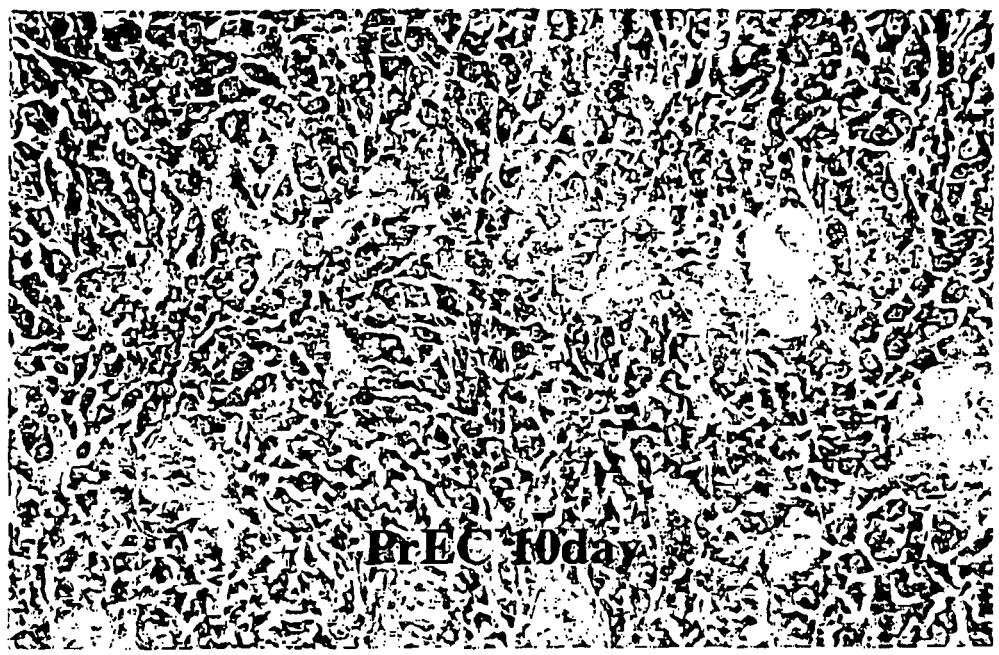
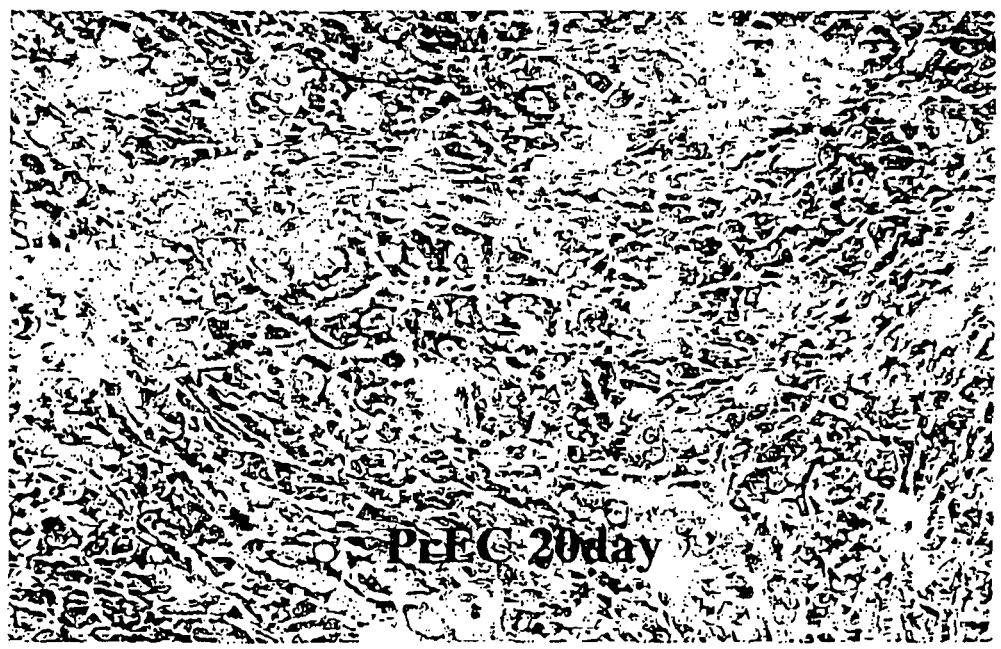

Fig 17
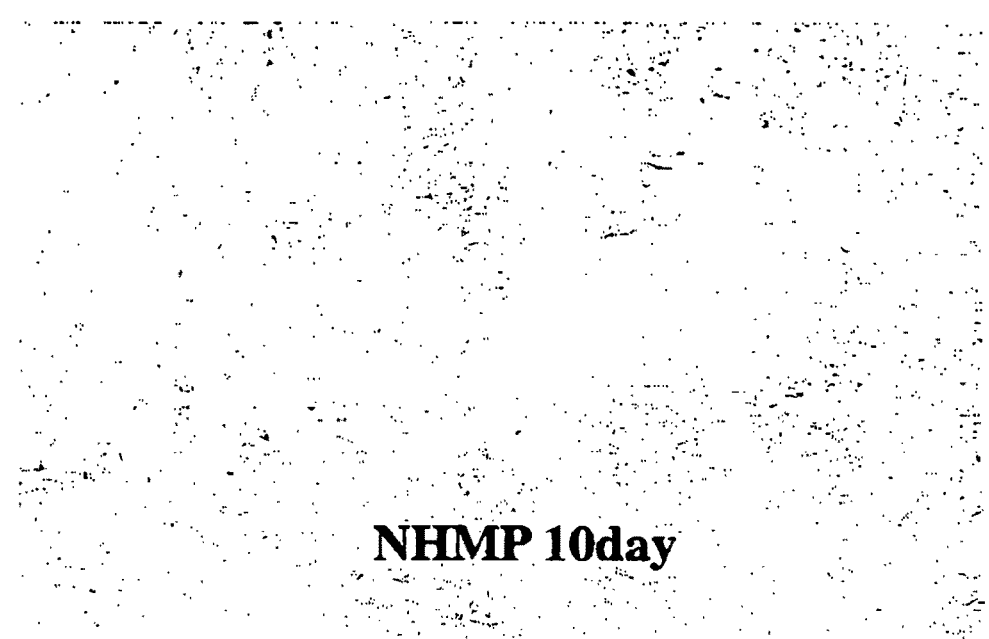
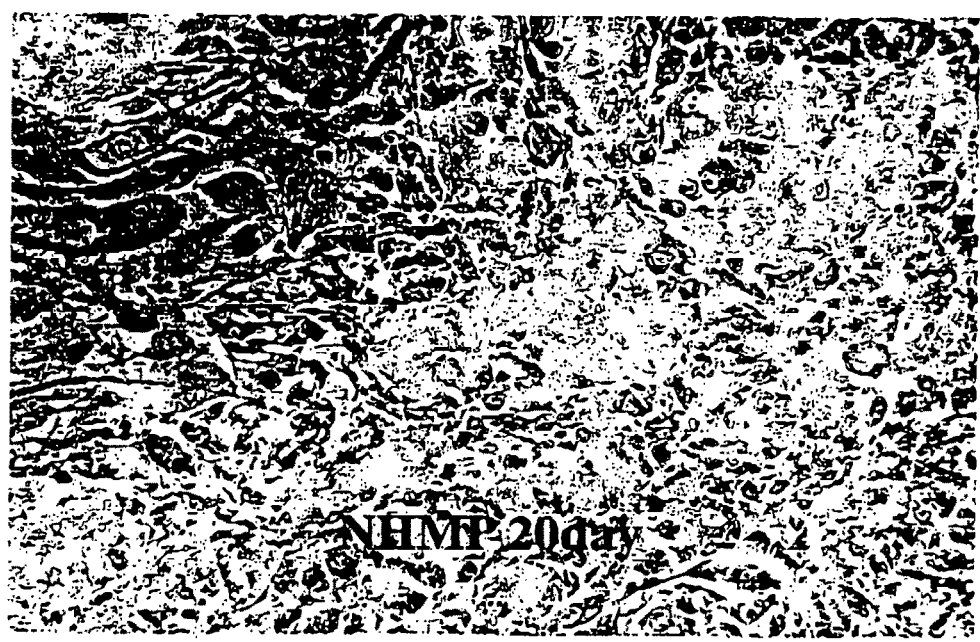

Fig 18
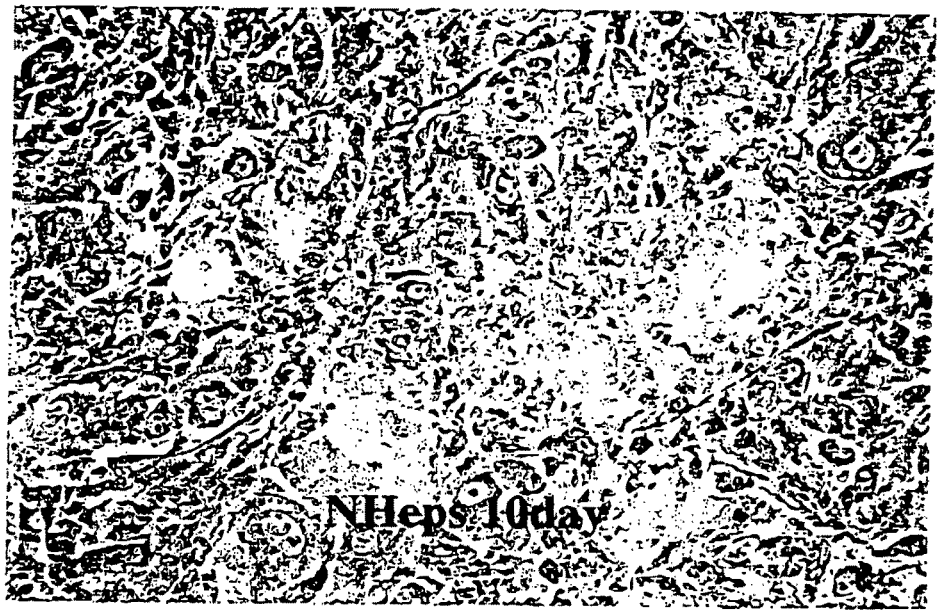
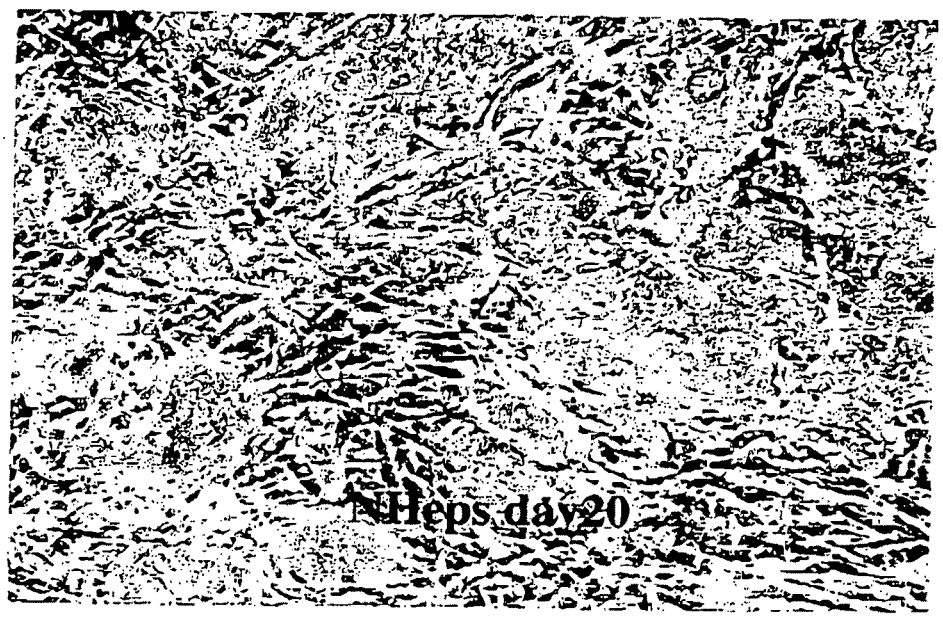

Fig. 1 9
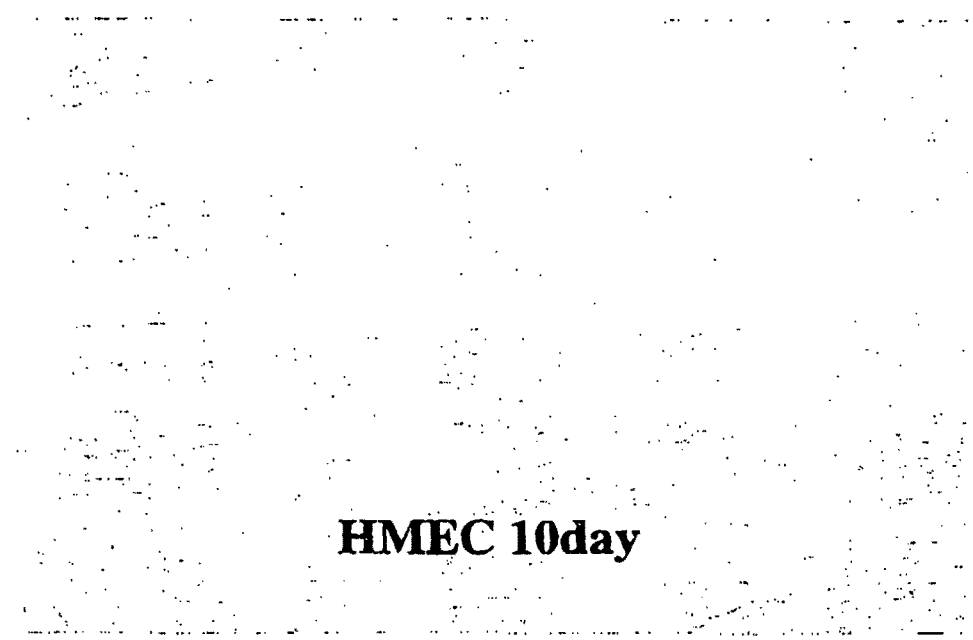
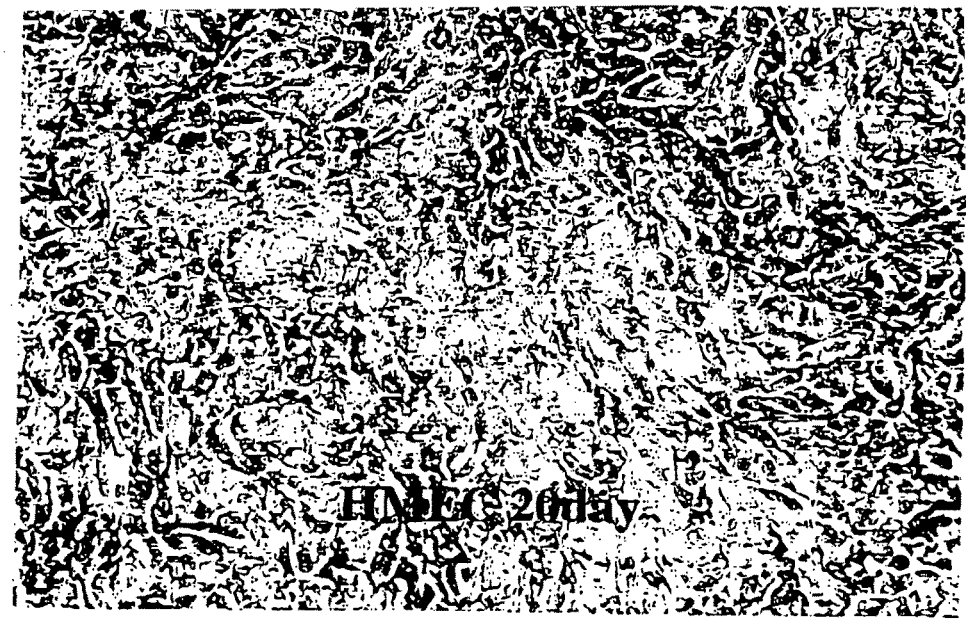

Fig 3 5
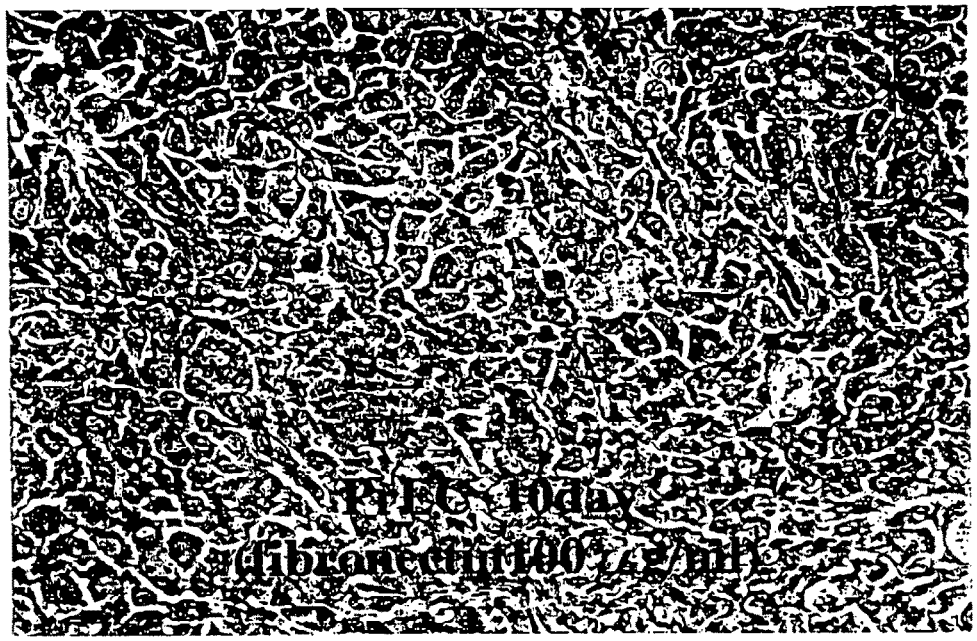
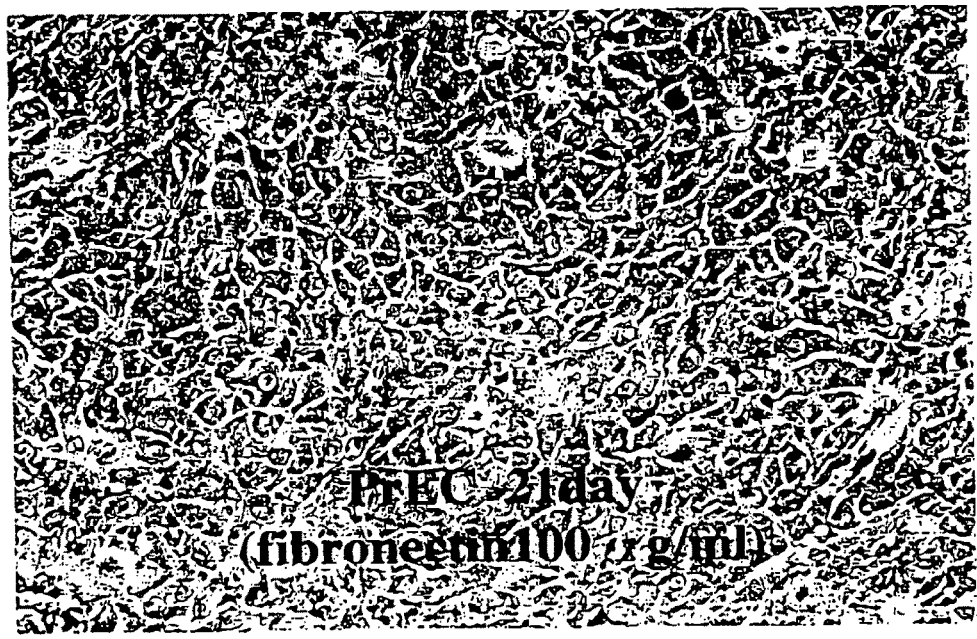

Fig 3 6
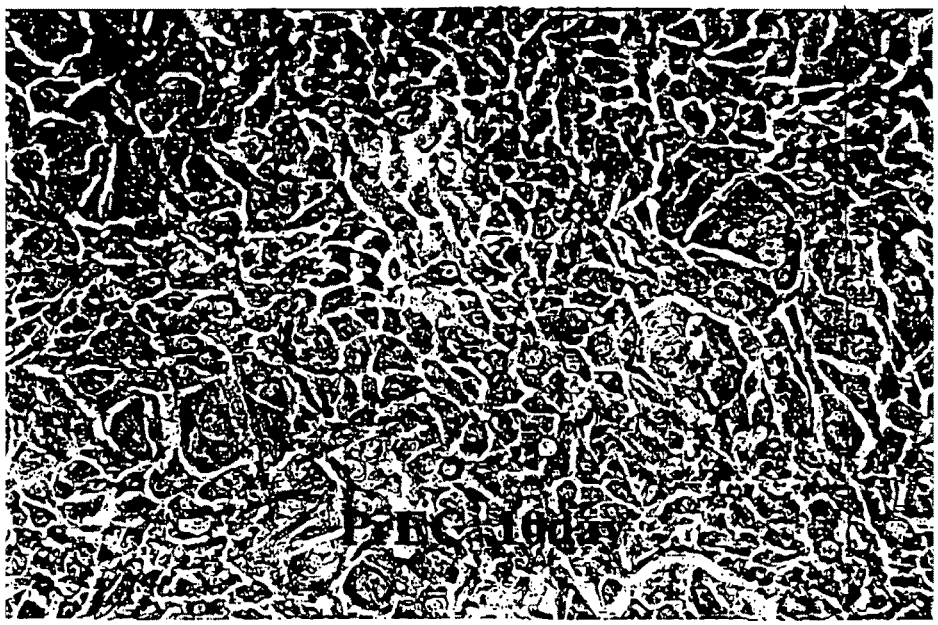
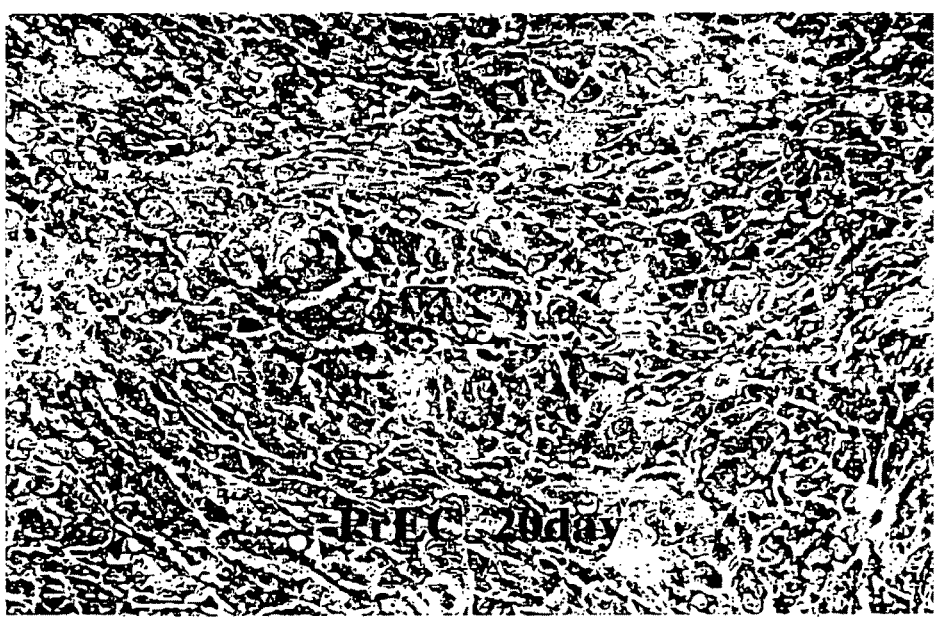

FIG. 37(a)
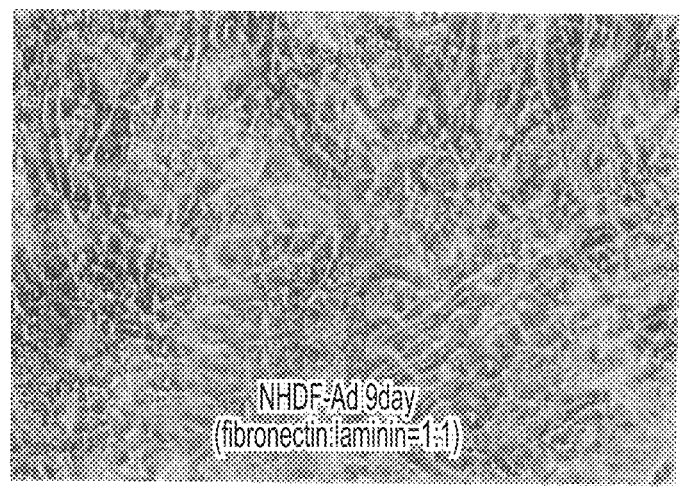
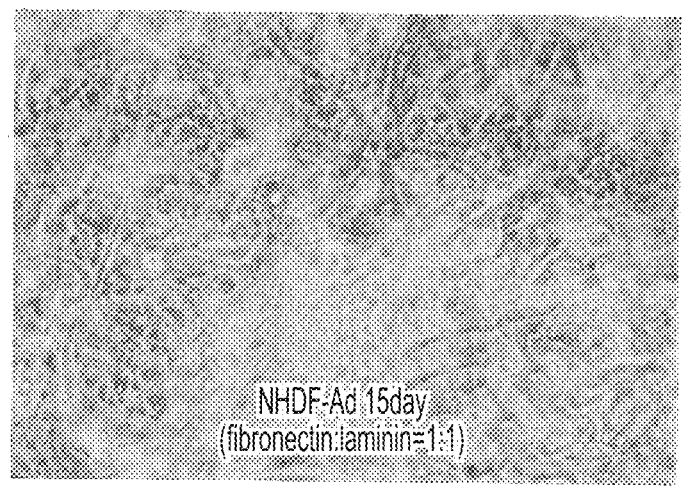

FIG. 37(b)

FIG. 38(a)
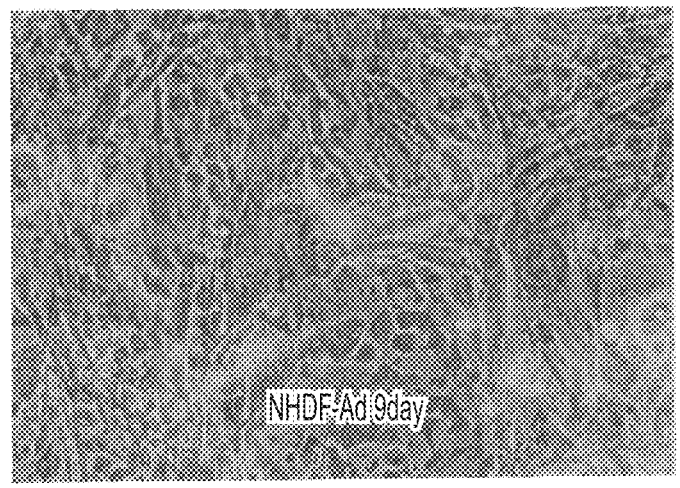
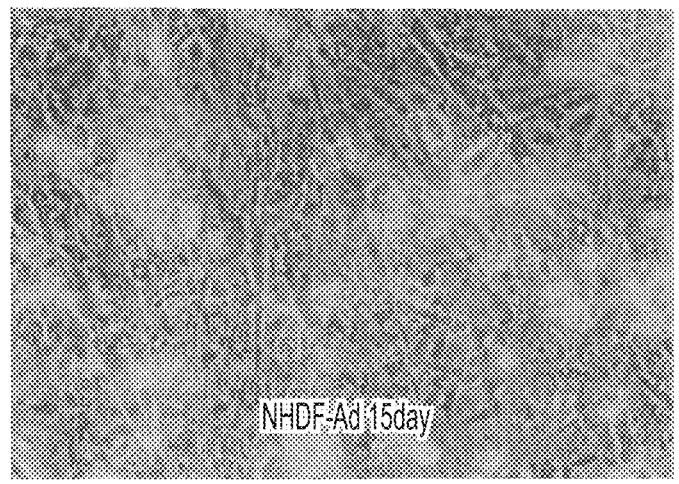

FIG. 38(b)
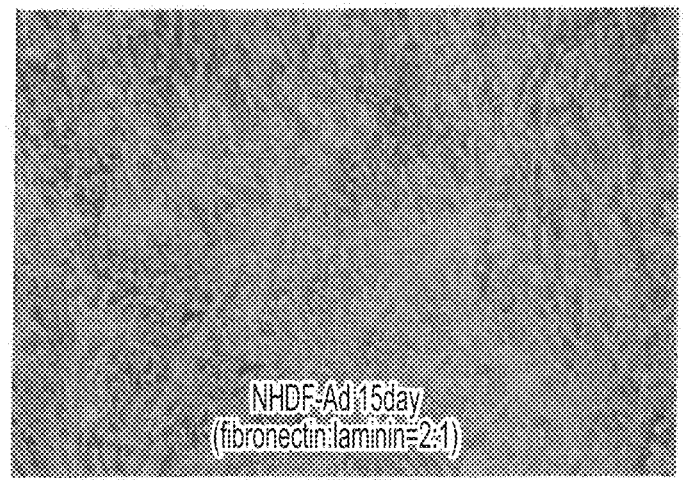
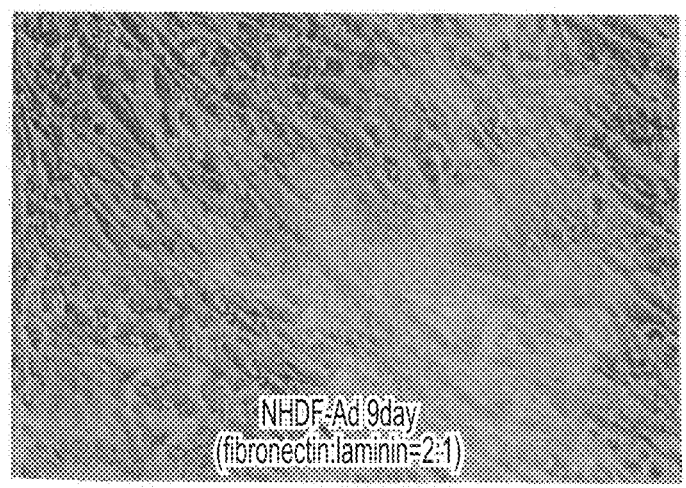

FIG. 39(a)
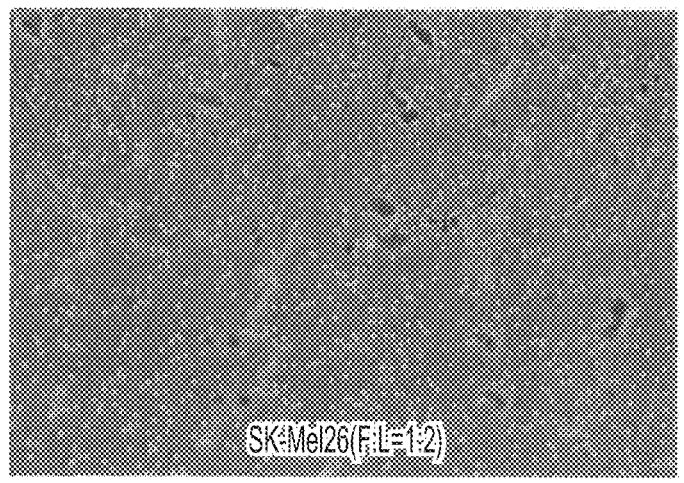
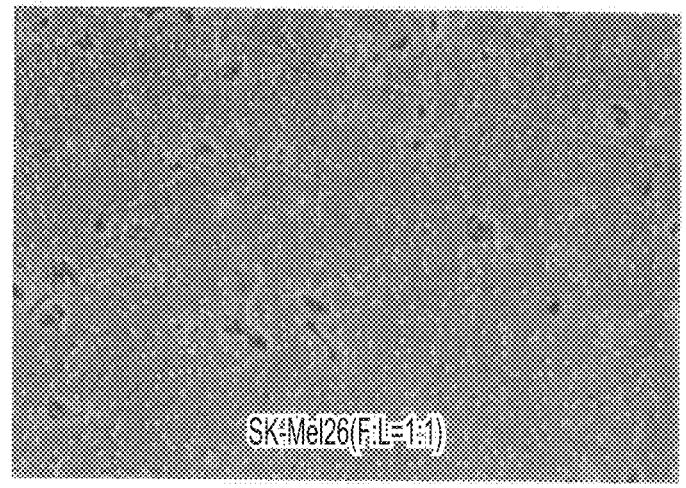

FIG. 39(b)
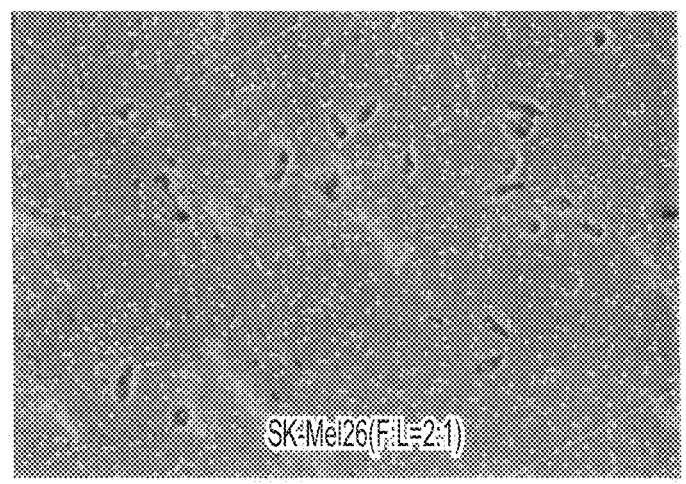
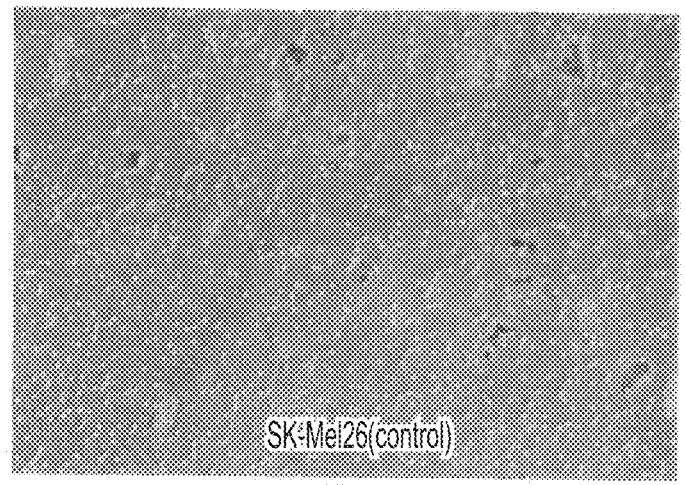

FIG. 40(a)
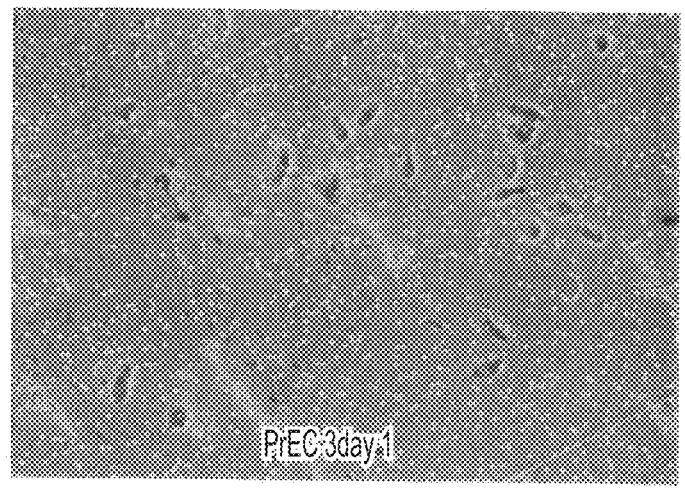
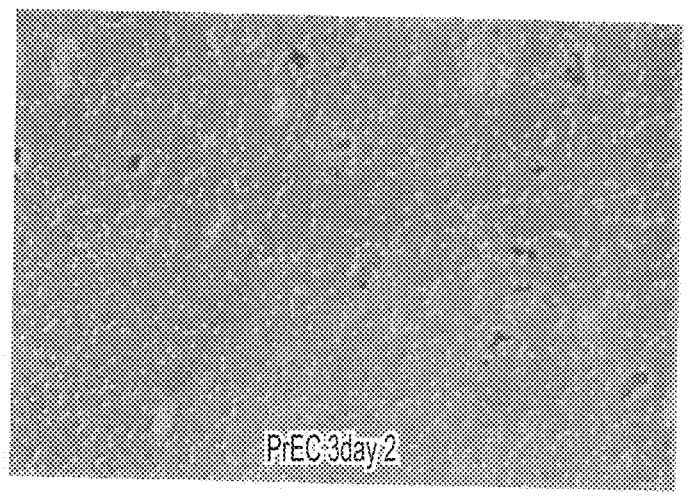

FIG. 40(b)
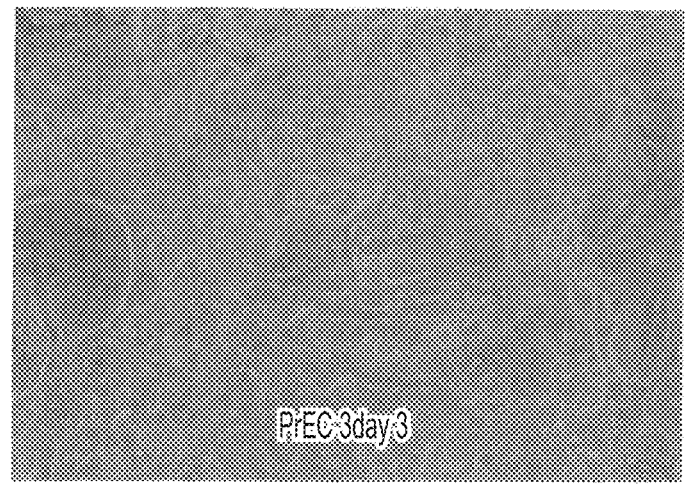
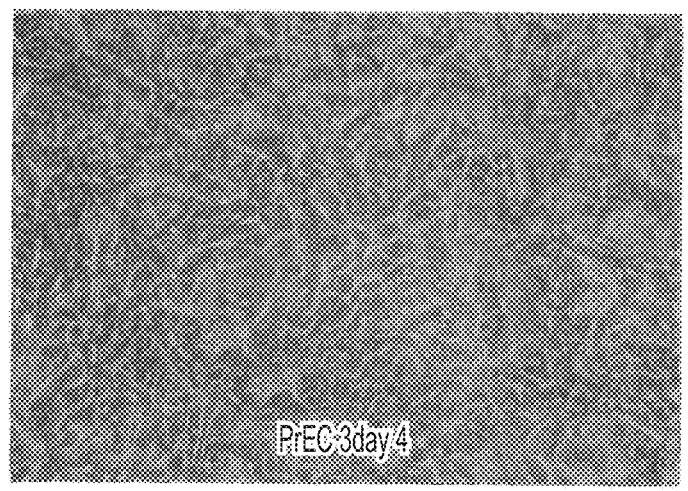

FIG. 41(a)
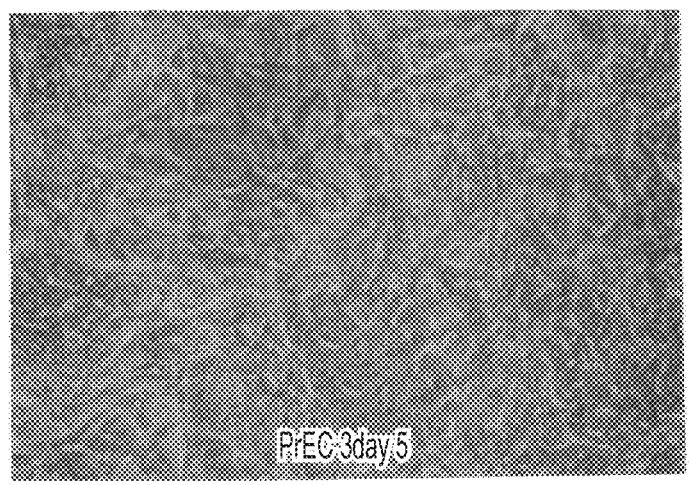
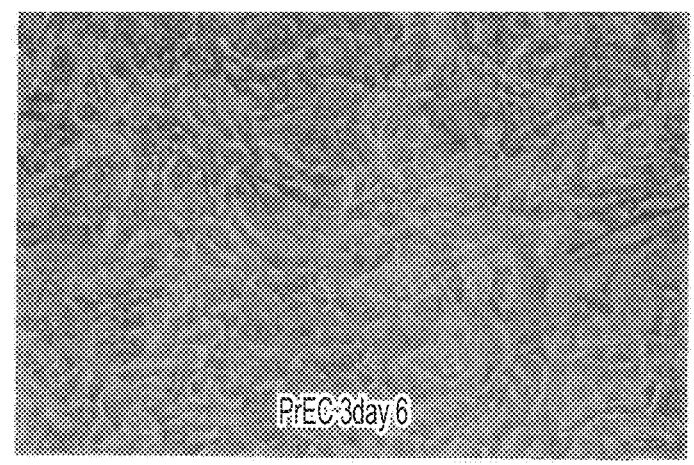

FIG. 41(b)
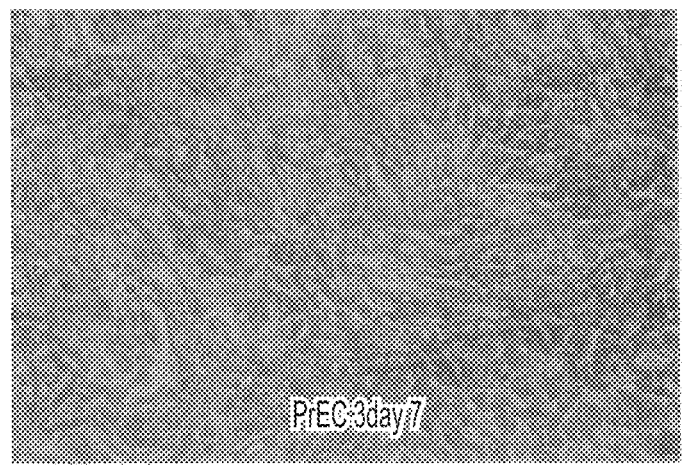
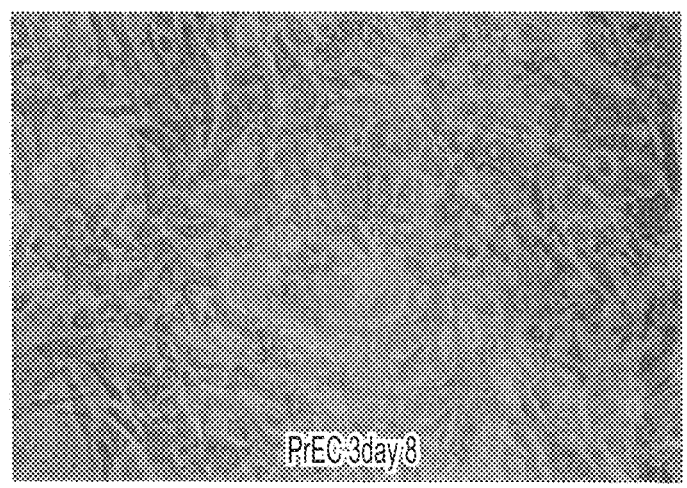

FIG. 42(a)
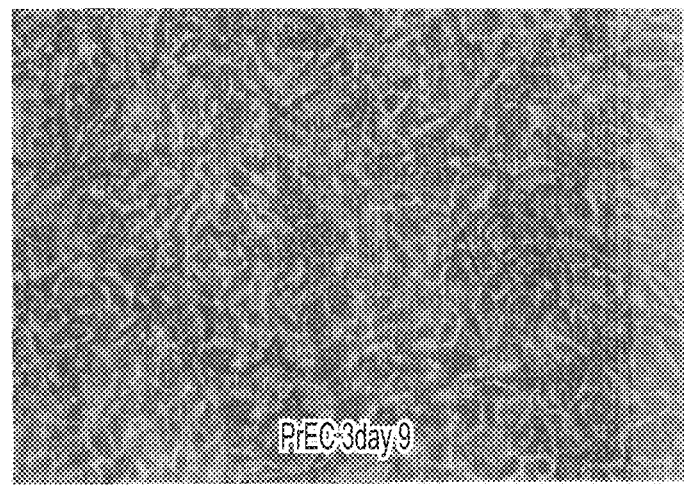
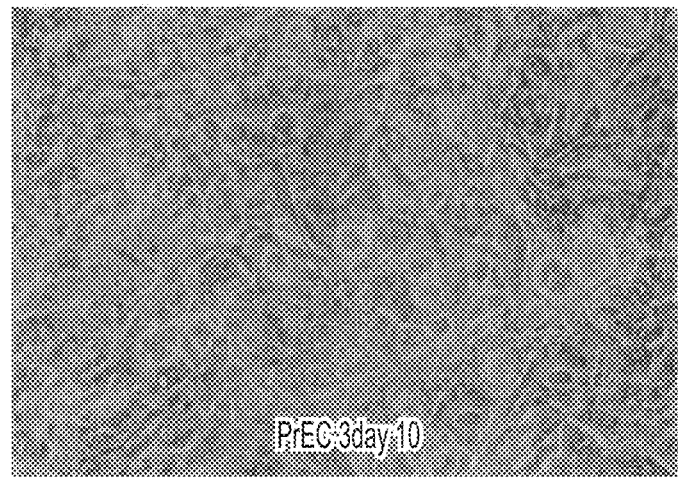

FIG. 42(b)
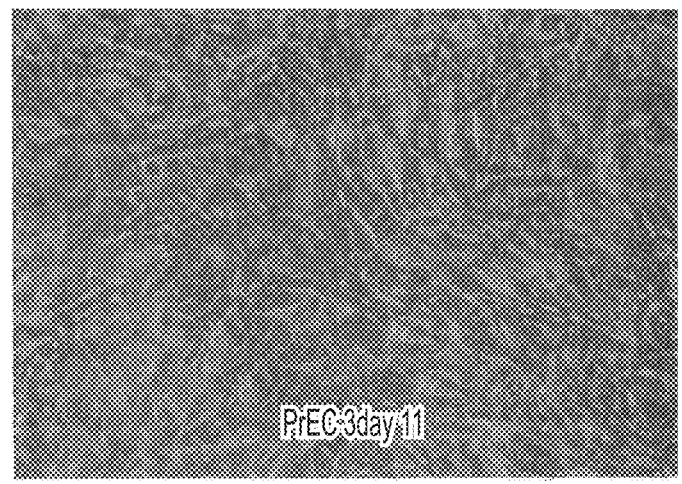
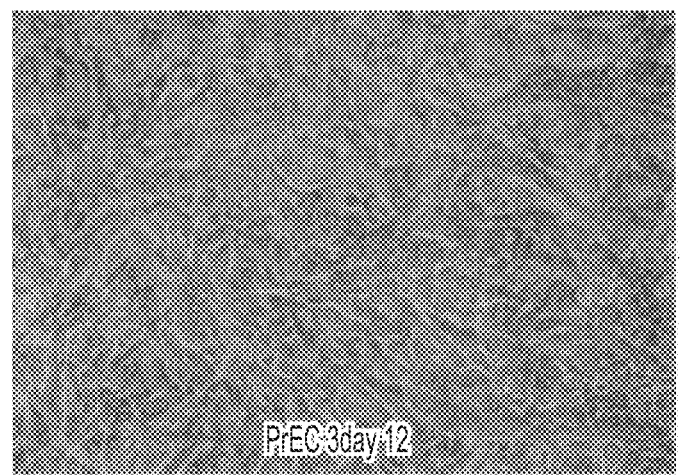

FIG. 46(a)
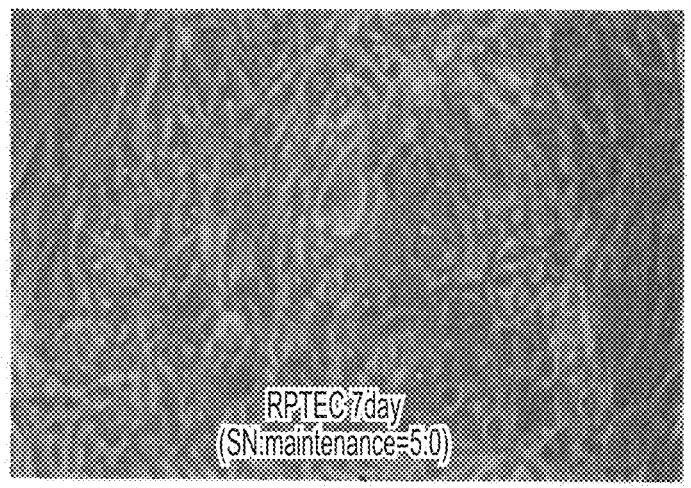
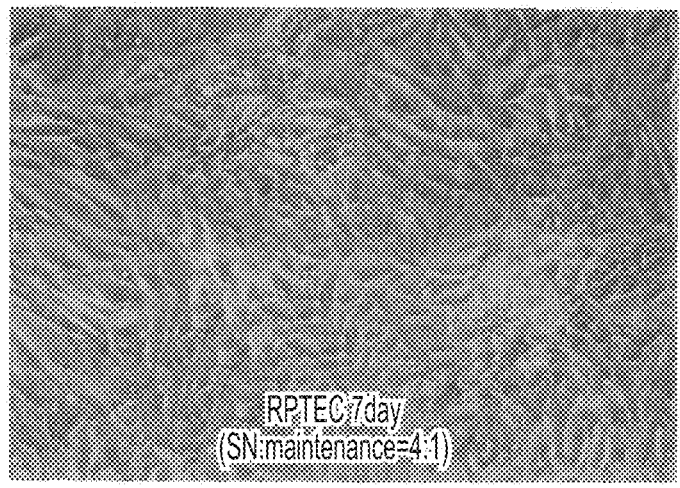

FIG. 46(b)
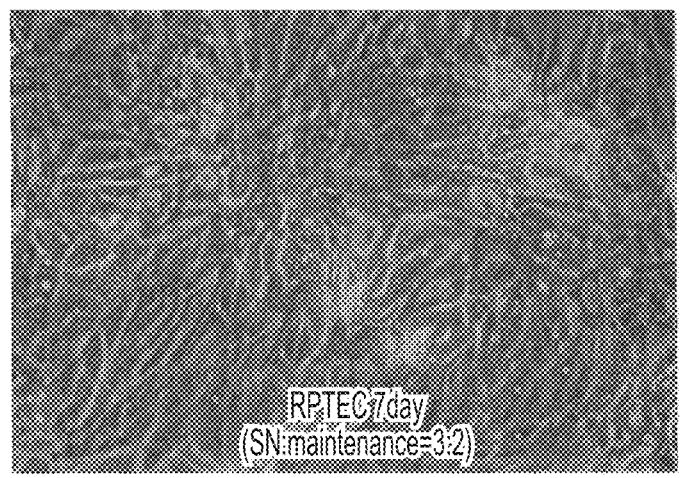
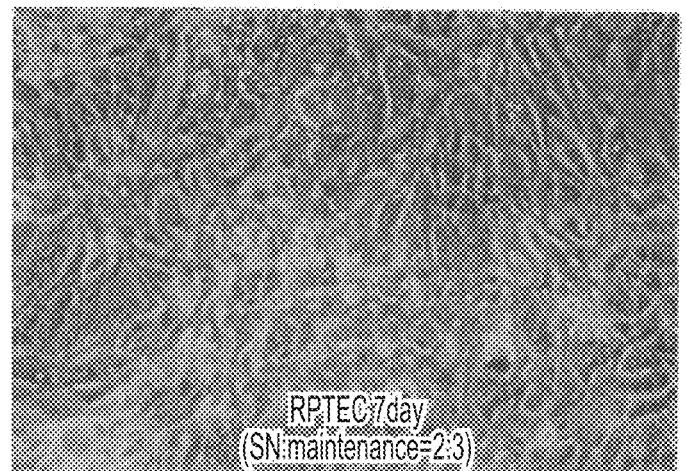

REGENERATED TISSUE COMPRISING A STRATIFIED STRUCTURE OF EPITHELIAL CELLS

TECHNICAL FIELD

The present invention relates to a method for forming a normal regenerated tissue, a normal regenerated tissue and a method for assessing sensitivity and the like.

BACKGROUND ART

While organ transplantation even after a cerebral death has not readily is put into action in Japan, a 3-dimensional culture mainly of tissue stem (TS) cell is conducted constantly for the purpose of a regeneration medical care. A use even of embryonic stem (ES) cell will be initiated soon although its ethical aspect is limited actually. Nevertheless, any of these technologies is far from the achievement of regenerated organ capable of exerting functions sufficiently. On the other hand, a human organ and tissue bank is attempted to be established and maintained as an opponent to a genome-derived pharmaceutical developed by manufacturers of medicines. Under such a circumstance, a formation of regenerated tissue by stratifying human-derived normal tissues and inducing a differentiation in a more simple and reliable manner when compared with a prior art is expected greatly and its realization is a significant objective, since a system for predicting the effects and the side effects of, or a system for assaying the sensitivity to a chemical substance mainly for a pharmaceutical can be constructed by obtaining a relevant organ model from the respective regenerated tissue.

Among current systems for assaying the effects of or the sensitivities to pharmaceuticals, a histoculture drug response assay (HDRA) using a collagen gel is known as a relatively effective means.

However, the HDRA has a problematically lower clinical true positive rate which is less than about 60%. Since the HDRA has a true negative rate of 80% or more, it is employed in a medical care practice only for screening for a non-effective anti-cancer agent in US. It is not regarded to be a recognized custom-made therapy which allows a most effective drug to be selected. Nevertheless, it is regarded as a highly advanced medical technology in Japan, although most of clinical practitioners are disappointed by the fact that it can select an effective drug at a probability as low as about 50%.

It fails also in assaying any side effect on normal tissues simultaneously.

A known method other than the HDRA is a CG-DST (collagen gel droplet embedded culture sensitivity test). However, this method involves cancer cells growth failure (no growth even in control) as high as 25% or more and gives an unsuccessful result at a rate as seriously high as 30% or more including the contamination rate, although its true positive rate is improved markedly to a level as high as 70 to 83%. Thus, when multiplying these two rates, the sensitivity can eventually be assayed only in 60% of the patients. Also from the data of the ovarian cancer, the assumption may vary depending on the tissue types. The potency of any side effect on normal tissues cannot be assayed also by this method.

Accordingly, any of the cancer therapy sensitivity tests of the prior art cannot predict the side effects on normal tissues simultaneously, even if it can evaluate the sensitivity of cancer cells or tissue to a therapy. It is far from an ideal custom-made therapy enabling the selection of a drug having fewer side effects.

Also in view for example of the current state described above, an assumption of the effects of and the sensitivity to a pharmaceutical should be enabled as soon as possible by obtaining a high level detection and evaluation system using regenerated tissues.

Accordingly, an objective of the invention is to overcome the limitations and the problems associated with the prior art described above, to obtain regenerated tissues simply and reliably by a 3-dimensional culture from a human-derived normal tissue as a base, and to provide, while utilizing the formers, a method for constructing a system for predicting the effects and the side effects of a chemical substance such as a pharmaceutical using thus regenerated tissues as a respective organ model or a system for predicting the sensitivity and the like.

DISCLOSURE OF INVENTION

For solving the problems described above, the invention provides a method for forming normal regenerated tissues comprising irradiating an organ-derived connective tissue or its constituent cells or supporting tissue to form a feeder layer followed by transplanting epithelial cells to form a stratified structure as a first aspect, a method for forming normal regenerated tissues wherein the connective tissue or its constituent cells or supporting tissue and the epithelial tissue are orthotopic with regard to the organ-derived as a second aspect, a method for forming normal regenerated tissues wherein the connective tissue or its constituent cells or supporting tissue are at least any of the organ-derived fibroblasts, endothelial cells or its constituent tissue as a third aspect, and a method for forming normal regenerated tissues wherein vascular endothelial cells are transplanted on organ-derived fibroblasts and then an irradiation is effected to form a feeder layer, and then the epithelial cells are transplanted to form a stratified structure as a fourth aspect.

The invention also provides a method for forming a normal regenerated tissue wherein after transplanting the epithelial cells at least one extracellular matrix is added to form the epithelial cells in a stratified structure as a fifth aspect, a method for forming a normal regenerated tissue wherein the extracellular matrix is a structural component or adhesion molecule of an extracellular substrate as a sixth aspect, a method for forming a normal regenerated tissue wherein the extracellular matrix is at least one of collagen, elastin, proteoglycan, fibronectin, laminin and tenascin as a seventh aspect, a method for forming a normal regenerated tissue wherein after transplanting a collagen or collagen with fibronectin as well as laminin are added to effect a gelatin whereby forming the epithelial cells in a stratified structure as the eighth aspect, a method for forming a normal regenerated tissue wherein the connective tissue or its constituent cells or supporting tissue is co-cultured with at least one of heterogenous constituent cells deriving from an orthotopic organ or a culture supernatant thereof and thereafter irradiated to form a feeder layer as a ninth aspect, a method for forming a normal regenerated tissue wherein heterogenous constituent cells deriving from an orthotopic organ, epithelial cells and a culture supernatant thereof is co-cultured to form a stratified structure as a tenth aspect, and a method for forming a normal regenerated tissue wherein the irradiation is an X-ray or γ-ray irradiation as an eleventh aspect, and a method for forming a normal regenerated tissue wherein the stratified structure of the epithelial cells are formed by a culture at a carbon dioxide gas concentration of 5 to 15%, air concentration of 85 to 95% at a culture temperature of 20 to 40° C. as a twelfth aspect.

The invention also provides a normal regenerated tissue comprising a stratified structure of epithelial cells on a feeder layer from an organ-derived connective tissue or constituent cells or supporting tissue as a thirteenth aspect, a normal regenerated tissue wherein the epithelial cells derive from nerve, oral mucosa, skin, bronchus, mammary gland, liver or kidney as a fourteenth aspect, a normal regenerated tissue wherein the connective tissue or its constituent cells or supporting tissue and the epithelial tissue are orthotopic with regard to the deriving organ as a fifteenth aspect, a normal regenerated tissue wherein the connective tissue or its constituent cells or supporting tissue are at least any of the organ-derived fibroblasts, endothelial cells or its constituent tissue as a sixteenth aspect, a normal regenerated tissue comprising a feeder layer consisting of organ-derived fibroblasts and vascular endothelial cells and epithelial cells in a stratified structure placed on the feeder layer as a seventeenth aspect, and a normal regenerated tissue wherein the epithelial cells are in a stratified structure consisting of four or more layers as a eighteenth aspect.

The invention also provides a normal regenerated tissue comprising a normal regenerated tissue placed on a basal plate as a nineteenth aspect, a normal regenerated tissue wherein a culture medium or culture fluid is allowed to flow in contact with a normal regenerated tissue as a twentieth aspect, a normal regenerated tissue wherein a plural of normal regenerated tissues are allowed to pass through the channel of the culture medium or culture fluid as a twenty first aspect and a normal regenerated tissue which constitutes regenerated organ model body as a twenty second aspect.

The invention also provides a method for assessing a sensitivity of cancer cells comprising inhibiting the proliferation of regenerated epithelial cells by irradiating any normal regenerated tissue described above followed by transplanting the cancer cells on the epithelial cells in a stratified structure followed by adding a chemical substance or irradiation as a twenty third aspect, a method wherein the assessment is effected at a low oxygen concentration as a twenty fourth aspect, a method comprising supplementing at least one of collagen or other extracellular matrixes after transplanting cancer cells or transplanting cancer cells after supplementing at least one of collagen or other extracellular matrixes, followed by assessing the sensitivity as a twenty fifth aspect.

The invention also provides a method for assessing an angiogenetic ability comprising inhibiting the proliferation of regenerated epithelial cells by irradiating any normal regenerated tissue described above followed by transplanting the cancer cells on the epithelial cells in a stratified structure followed by supplementing at least one of collagen or other extracellular matrixes on which then vascular endothelial cells are transplanted followed by assessing the angiogenetic ability of the cancer cells in response to the addition of a chemical substance as a twenty sixth aspect.

The invention also provides a method for assessing an angiogenetic ability comprising inhibiting the proliferation of regenerated epithelial cells by irradiating a normal regenerated tissue followed by transplanting the cancer cells on the epithelial cells in a stratified structure followed by mounting at least one of collagen or other extracellular matrixes followed by inverting the entire structure whereby assessing a motility or invasion ability for the purpose of evaluating the effect of a metastasis or invasion inhibitor as a twenty seventh aspect.

The invention also provides a method for assessing a sensitivity of a normal regenerated tissue comprising an exposure of the tissue to a chemical substance or irradiation as a twenty eighth aspect.

The invention also provides a method for assessing a gene transduction comprising predicting the efficiency of the gene transduction in a normal regenerated tissue as a twenty ninth aspect.

The invention also provides a method of any of those listed above wherein the irradiation for inhibiting the proliferation of regenerated epithelial cells are an X-ray or γ-ray irradiation as a thirtieth aspect.

BRIEF DESCRIPTION OF DRAWINGS

FIG. 10 is a microscopic photograph showing the condition of a regenerated bronchial epithelial cell layer formed by an inventive method which had been supplemented with a collagen gel and then transplanted with human pulmonary cancer-derived AOI cells after three days;

FIG. 11 is a microscopic photograph showing the condition immediately after the X-ray irradiation at 20GY 3 hours after the transplantation similar to that in FIG. 10;

FIG. 12 is a microscopic photograph showing the condition 3 days after the irradiation in the case shown in FIG. 11;

FIG. 13 is a microscopic photograph showing the condition after the X-ray irradiation at 10Gy in the case shown in FIG. 12;

FIG. 14 is a microscopic photograph of renal proximal tubular epithelial cells (RPTEC) in a stratified structure in Embodiment 2;

FIG. 15 is a microscopic photograph of mesangium cells (NHMC) in a stratified structure;

FIG. 16 is a microscopic photograph of prostatic epithelial cells (PrEc) in a stratified structure;

FIG. 17 is a microscopic photograph of neural progenitor cells (NHMP) in a stratified structure;

FIG. 18 is a microscopic photograph of human hepatocytes (NHeps) in a stratified structure;

FIG. 19 is a microscopic photograph of mammary gland epithelial cells (HMEC) in a stratified structure;

FIG. 35 is a microscopic photograph of PrEc regenerated in a stratified structure with adding only a collagen in Embodiment 4. On the other hand, FIG. 36 is a microscopic photograph using only a fibronectin without using a collagen;

FIGS. 37(a) and 37(b) are microscopic photographs obtained when adding a 1:1 or 1:2 mixture of a fibronectin and laminin to a collagen when regenerating NHDF-Ad: human skin keratinized cells in a stratified structure on a feeder layer of human skin-derived fibroblasts;

FIGS. 38(a) and 38(b) are microscopic photographs obtained when adding only a collagen or adding a 2:1 mixture of a fibronectin and laminin;

FIGS. 39(a) and 39(b) are microscopic photographs obtained when adding a collagen together with a fibronectin and laminin in human melanoma-derived SK-Mel26 cells invasion test of NHDF-Ad regenerated as a stratified structure in Embodiment 6;

FIGS. 40(a), 40(b), 41(a), 41(b), 42(a) and 42(b) are microscopic photographs exemplified as Cases 1 to 12 showing the effects of the addition of the fibronectin and laminin to the collagen in the PrEC culture as a stratified structure in Embodiment 7;

FIGS. 46(a)-46(c) are microscopic photographs exemplifying the change in the sensitivity discussed above.

BEST MODE FOR CARRYING OUT THE INVENTION

Figure 1:
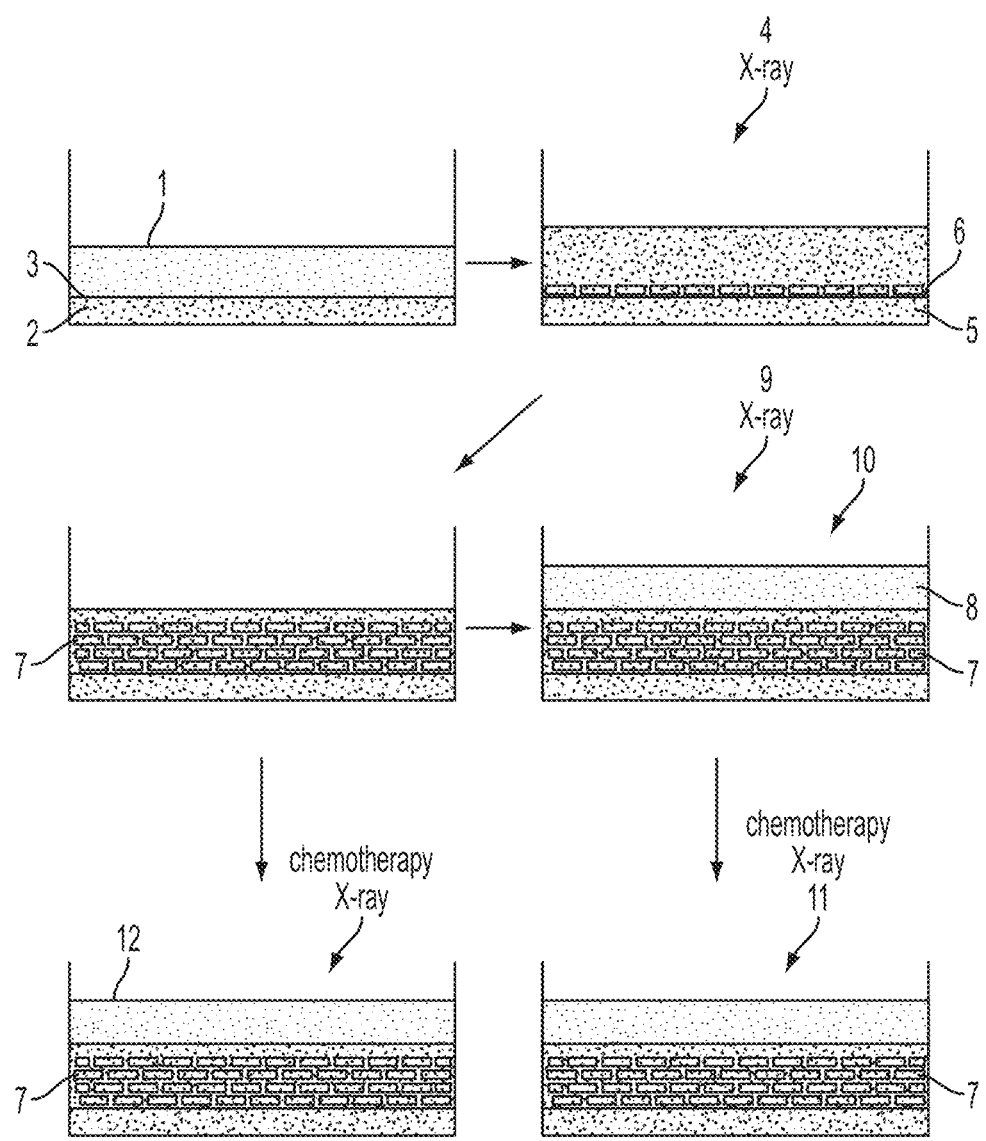
FIG. 1 is an outline exemplifying an inventive method.

The present invention is characterized as described above, and its embodiments are described below.

First, for describing the background of the invention briefly, the significance of the orthotopic transplantation has been emphasized by J. Fiedler in MD Anderson Cancer Center in 1970's and later through the studies especially of cancer metastasis and spread all over the world. Thus, in a lung, there is an environment generated as a result of a homeostasis attributable to lung-specific growth factors or humoural factors such as cytokines as well as an adhesion between cells. Accordingly, it has been suggested that "under such an environment, lung-derived cells such as fibroblasts can exert their natural trait most evidently". Recently, his team rather reported that a fibroblast derived from each organ underwent a mutation specific thereto thus being different from each other. While this report has not been accepted widely, another recent report suggested that a subculture resulted in the induction of p16 in a pulmonary fibroblast but not in a dermal fibroblast.

While taking these findings into account, we provide a far more efficient novel 3-dimensional culture method when compared with conventional 3-dimensional methods employing an endogenous virus-carrying mouse-derived NIH3T3 cell as a feeder layer (FL) or employing only a collagen gel which is a ubiquitous extracellular matrix. Our method utilizes the nature of the orthotopic transplantation described above while taking advantage of the fact that cancer cells can not keep existing exclusively in a living body without any normal tissue, the fact that almost no noise is generated in a gene expression profile by irradiated cells or FL, the fact that normal (epithelial) cells, apart from cancer cells, hardly undergoes a proliferation in a stratified structure usually on a gel, and the fact that irradiated cells or FL causes a negligible noise on an MTT assay.

Thus, the present invention is characterized by irradiating an organ-derived connective tissue or its constituent cells or supporting tissue to form a feeder layer followed by transplanting epithelial cells to form a stratified structure, and in this case it is a matter of course that the connective tissue or supporting tissue is a producer of a growth factor or cytokine.

A representative which plays a role of a connective tissue or its constituent cells or supporting tissue may for example be organ-derived fibroblasts, endothelial cells or its constituent tissue. Among those listed above, fibroblasts and vascular endothelia can be co-cultured in the invention. Otherwise, a glia cell, smooth muscle cell or a muscle such as a myocardium can be mentioned.

Especially in the invention, it is an important embodiment that a connective tissue or its constituent cells or supporting tissues and epithelial cells are orthotopic with regard to the deriving organ, which is thus an identical skin, kidney, bronchus, nerve and the like. Such an orthotopicity ensures an efficient formation of a stratified structure of the epithelial cells.

More typically, the invention provides a method for forming a normal regenerated tissue wherein vascular endothelial cells are transplanted on organ-derived fibroblasts in a medium and then an irradiation is effected to form a feeder layer, and then the epithelial cells are transplanted to form a stratified structure.

An inventive method is characterized also in that after transplanting the epithelial cells at least one extracellular matrix is added to form the epithelial cells in a stratified structure, and also in that the extracellular matrix is a structural component or adhesion molecule of an extracellular substrate, more typically at least one of collagen, elastin, proteoglycan, fibronectin, laminin and tenascin. Moreover, the strafing efficiency is improved further by adding growth factors derived from each organ.

In a preferred embodiment, a collagen or collagen with fibronectin as well as laminin are added after transplanting to form the epithelial cells in a stratified structure, or the irradiation is an X-ray or γ-ray irradiation. Furthermore, it is also preferable that the connective tissue or its constituent cells or supporting tissue is co-cultured with at least one of a heterogenous constituent cells deriving from an orthotopic organ or a culture supernatant thereof and thereafter irradiated to form a feeder layer, that heterogenous constituent cells deriving from an orthotopic organ, epithelial cells and a culture supernatant thereof are co-cultured to form a stratified structure, and that the stratified structure of the epithelial cells are formed by a culture at a carbon dioxide gas concentration of 5 to 15%, air concentration of 85 to 95% at a culture temperature of 20 to 40° C.

According to an inventive method described above, a normal regenerated tissue comprising a stratified structure of epithelial cells on a feeder layer from an organ-derived connective tissue or constituent cells or supporting tissue is obtained.

In such a case, the epithelial cell layer may be of any type, such as those deriving from nerve, oral mucosa, skin, bronchus, mammary gland, liver or kidney.

According to the invention, the stratified structure consisting of three, four, five or more layers, i.e., about four or more layers is readily available. The resultant normal regenerated tissue may be placed on a basal plate, or may be one wherein a culture medium or culture fluid is allowed to flow in contact with a normal regenerated tissue or one which constitutes regenerated organ model body.

Also according to the invention, a method for predicting a sensitivity of cancer cells comprising inhibiting the proliferation of regenerated epithelial cells by irradiating a normal regenerated tissue followed by transplanting the cancer cells on the epithelial cells in a stratified structure followed by adding a chemical substance or irradiation, and its typical example which is a method wherein the prediction is effected at a low oxygen concentration as well as a method comprising supplementing at least one of collagen or other extracellular matrixes after transplanting cancer cells or transplanting cancer cells after supplementing at least one of collagen or other extracellular matrixes, followed by assessing the sensitivity are provided.

Moreover, a method for predicting an angiogenetic ability comprising inhibiting the proliferation of regenerated epithelial cells by irradiating a normal regenerated tissue followed by transplanting the cancer cells on the epithelial cells in a stratified structure followed by supplementing at least one of collagen or other extracellular matrixes on which then vascular endothelial cells are transplanted followed by predicting the angiogenetic ability of the cancer cells in response to the addition of a chemical substance, a method for predicting an angiogenetic ability comprising inhibiting the proliferation of regenerated epithelial cells by irradiating a normal regenerated tissue followed by transplanting the cancer cells on the epithelial cells in a stratified structure followed by mounting at least one of collagen or other extracellular matrixes followed by inverting the entire structure whereby assessing a migrating or invasion ability, a method for assessing a sensitivity of a normal regenerated tissue comprising an exposure of the tissue to a chemical substance or irradiation, and a method for assessing a gene transduction comprising assessing the efficiency of the gene transduction in a normal regenerated tissue are provided.

The embodiments of the invention are exemplified below with referring to the attached figures which outline the invention.

Embodiment 1

For example with regard to a system for assessing sensitivity, a multiwell dish such as 6-well, 12-well or 24-well dish may be employed. First, fibroblasts and vascular endothelial cells derived from an intended organ is isolated from a surgically excised tissue by means of a treatment with a collagenase and trypsin in a mild manner such that the bulk of cells are not separated into individual cells and then identified using a monoclonal antibody, cell sorter and the like. Then, for example as shown in FIG. 1, a 15% fetal calf serum-supplemented maintenance medium (1) is used to inoculate about $0.5 \times 10^5$ cells/cm$^2$ of the fibroblasts (ratio: 10) (2) with the vascular endothelial cells (ratio:1) (3), which is then irradiated within the period of about 6 to 24 hours with a preconditioning dose (20Gy or less) of an X-ray (4) for maintaining the tissue structure as a fundamental layer over about 2 weeks while suppressing the proliferation of the fibroblasts to form an FL (5).

On this FL (5), epithelial cells layer (about $1.0 \times 10^5$ cells/cm$^2$) (6) separated from the identical excised tissue by a mild disperse treatment is transplanted. The epithelial cells (6) are going to be stratified 3-dimensionally to become a regenerated epithelium (7). When the donor is an elderly human or a human having a heavily smoking history, the top layer was covered with a sterilized and ice-cold liquid collagen (8) [prepared by diluting with a medium supplemented with relatively low levels of various growth factors (the growth factors at concentrations as low as about ½ or less of the levels in the maintenance medium)], which was then gelled by warning the temperature for example to 37° C. When maintaining the regenerated tissue, the carbonate gas level is elevated slightly when compared with an ordinary level, such as 10%, and the culture is conducted at an air level of 90% at 37° C. Also cocultured are a carbonate gas level of 5 to 15%, air level of 85 to 95% and a temperature of 20 to 40° C. During this culture, the culture medium is replaced for example three times a week. At the time point within about 2 weeks when the stratified structure acquired about 4 layers or more i.e., 4 layers or 3 layers or more, the major effects, side effects or toxic effects on a normal tissue are evaluated after the treatment with various combinations of chemicals at respective concentrations or within about several hours to 24 hours after the irradiation using an MTT assay, gene expression profile or protein profile.

Table 1 shows the compositions of a medium assayed to be employed before the step for forming a stratified structure such as an NHBH (e.g., for mammary gland epithelium or bronchial epithelium) and a high-factor NHBE (for a special growth promotion of bronchial epithelium and the like) and a medium assayed to be employed in forming a stratified structure such as the maintenance medium.

TABLE 1

|  | Total volume of maintenance medium 420 ml | NHBE | High-factor NHBE |
|---|---|---|---|
| F-12 | 100 ml/420 ml |  |  |
| Transferrin | 5.0 µg/ml | 10 µg/ml | 10 µg/ml |
| Insulin | 5.0 µg/ml | 5 µg/ml | 5 µg/ml |
| Hydrocrtizon | 0.4 µg/ml | 0.5 µg/ml | 0.5 µg/ml |
| Triiodothyronin | $2 \times 10^{-9}$ M | $6.51 \times 10^{-9}$ M | $6.51 \times 10^{-9}$ M |
| h-EGF | 0.05 µg/ml | 0.005 µg/ml | 0.05 µg/ml |
| choleratoxin | $1 \times 10^{-9}$ M |  | $1 \times 10^{-9}$ M |
| BSA-FAF |  | 0.02 mg/ml | 0.02 mg/ml |
| BPE |  | 7.5 µg/ml | 7.5 µg/ml |
| Epinephrine |  | 0.5 µg/ml | 0.5 µg/ml |
| Retinoic Acid |  | 0.1 ng/ml | 0.1 ng/ml |
| GA-1000 |  | Gentamycin 50 µg/ml Amphotericin B 0.05 µg/ml | Gentamycin 5 µg/ml Amphotericin B 0.05 µg/ml |
| CaCL$_2$ |  |  |  |
| BSA |  |  |  |
| Ascolbic Acid |  |  |  |
| FCS |  |  |  |
| FBS | 5% |  |  |

The invention also provides a normal regenerated tissue panel or chip constructed by a characteristic 3-dimensional culture as well as a regenerated organ model body.

On a basal plate of a hard glass or quartz, a regenerated tissue described above is formed, and its culture medium is allowed to flow. Multiple types of normal regenerated tissues can be in communication with each other as a channel for the culture medium. In the case of a panel or chip, the surface of the basal plate may be coated with a substrate such as laminin or fibronectin.

We actually verified that it is possible to construct a normal regenerated tissue derived from the organs listed in Table 2 as well as a normal regenerated tissue derived from nerve, skin, mammary gland, liver, kidney and the like.

TABLE 2

Trachea and bronchia

1) Mucosa
Epithelium: Non-ciliated cell, Ciliated cell, Goblet cell, Basal cell, Neurosecretory cell, Intermediate cell
Tunica propria: Collagen fiber, Elastica, Fibroblast, Blood capillary
Submucosa
2) Tracheal gland (Bronchial gland)
Myxocyte, Serous cell
3) Terminal bronchiole
Ciliated cell, Clara cell
Alveoli 1) Alveolar septum
Supporting tissue, Elastica, Collagen fiber, Cancellous fiber, smooth muscle
Cells in alveoli: Interstitial cell (septal cell), fobrous cell, Contractile interstitial cell, phagocyte, mast cell, blood-derived cell
2) Alveolar pore
3) Blood capillary, Blood capillary pore, Endothelium, Pericyte
4) Alveolar epithelium
Type I alveolar epithelium (alveolar squamous cell)
Type II alveolar epithelium (large alveolar epithelium)
Alveolar brush cell Each panel or chip can be used as an organ model, which can be an established means for detecting the major effects and side effects of a chemical such as a drug as well as an extract such as a hormone. Until now, commercially available bronchus, kidney, mammary gland, prostate, liver, nerve and skin or patient-derived cervical mucosa obtained as cells with an informed consent have been subjected to a 3-dimensional culture and the regeneration of all tissues derived from various organs has been accomplished successfully. When all organs including heart and liver targeted by a drug and the like will be investigated, an application to a panel for assessing the major and side effects of the drug will be enabled. It is a matter of course that an application to a means for testing the sensitivity to an anti-cancer agent may be possible.

By mixing the medium compositions for various panels and chips, a comfortable chemical assessment system will be established which does not only handle endocrinal hormones or autocrine or paracrine growth factors but also handles nerves in near future.

For example in the case where the sensitivity of an anticancer agent alone or in combination with various radiotherapy by various fractionations, a regenerated epithelium (7) in a stratified structure shown also in FIG. 1 is irradiated with a 20Gy or less or X-ray or γ-ray (9) for the purpose of suppressing its proliferation to form a novel FL, which is inoculated with cancer cells (at a density of about 1000 cells/cm$^2$) (10) which was separated from a surgical specimen, cut into 1-3 mm square pieces and then maintained in a collagen gel prepared in a conditioning medium for the FL described above or a normal fibrous tissue or with any other tissue containing a tumor interstitial material. Then the medium is replaced with a medium whose growth factor levels are as low as possible, and subjected to various treatments described above after about 12 to 24 hours, followed by an MTT assay after about 48 to 96 hours or gene expression profile, protein profile and the like after about 6 to 48 hours. When cancer cells (10) are added, then the collagen gel is supplemented as desired, and the addition of a chemical or an irradiation (11) may be employed to assess the sensitivity of the cancer cells. Then at the time point when the cancer tissue is grown 3-dimensionally to a 3-5 mm-cube size or more, the collagen gel is further mounted to establish an environment close to a low oxygen condition, and then vascular endothelial cells are transplanted on the outside of the collagen gel whereby enabling an application to the investigation of the angiogenetic ability of individual cancer species for the purpose of assessing an angiogenesis inhibitor. A known method for establishing a low oxygen condition in a culture medium may for example be a method which gives a spheroid cancer cell population which is proliferated in a spherical shape like a green alga ball by a rotational culture. In such a case, when the diameter becomes about 200 to 400 micron or more, a low oxygen condition is established in the center. Based on these findings, it is possible also in the invention that a gel-encapsulated cancer tissue is proliferated 3-dimensionally to establish a low oxygen condition in its center. Also by mounting a gel formed from a type IV collagen and the like and then inverting the entire structure, an application to a system for investigating invasion ability for the purpose of assessing a motility or invasion inhibitor is possible.

Figure 2:
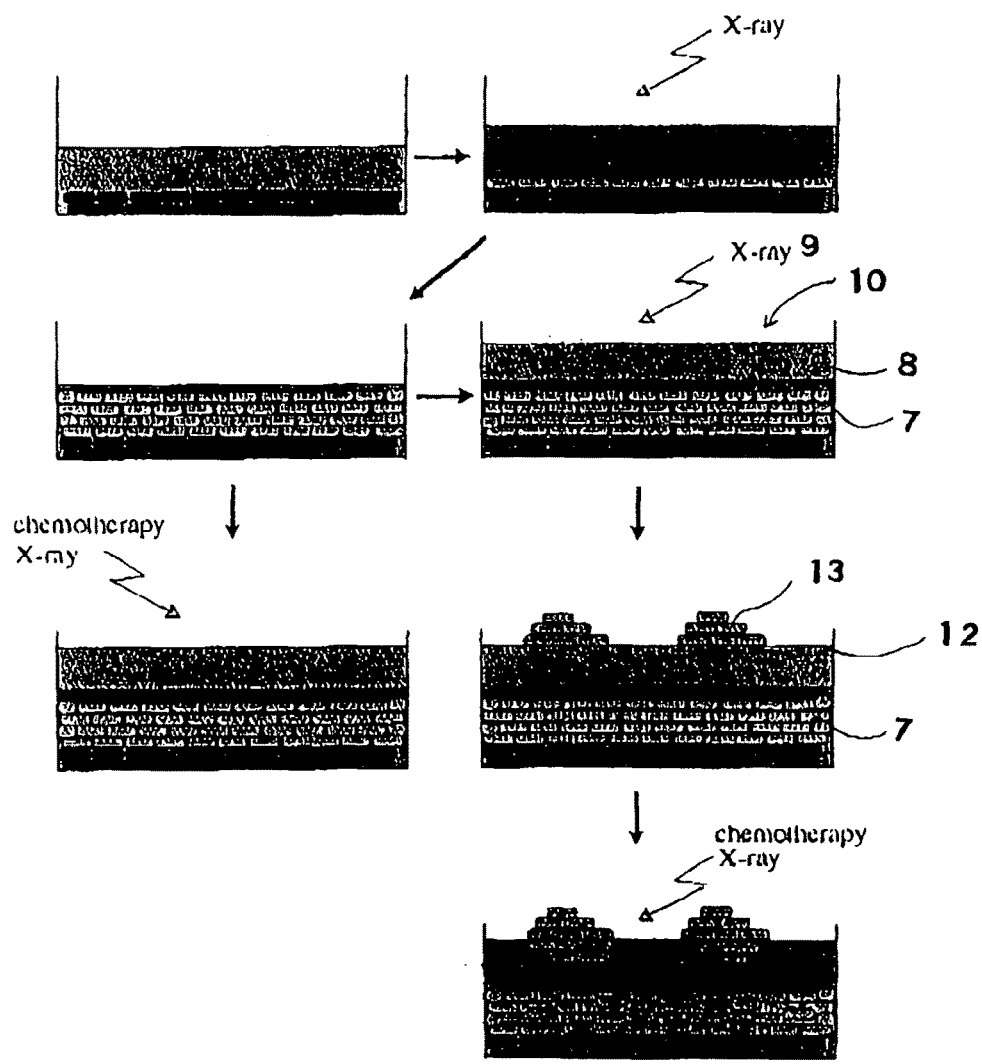
FIG. 2 is an outline exemplifying a method to be added to the process of FIG. 2.

Besides the assessment of the cancer cell sensitivity, a collagen gel (12) is supplemented on a epithelial cell layer in a stratified structure for example as shown in FIG. 2, and then covered with a cancer tissue (13), whereby enabling the assessment of the sensitivity of the cancer tissue to a chemical or irradiation.

On the other hand, a normal regenerated tissue having an epithelial cell (7) layer in a stratified structure shown in Figs. is supplemented if necessary with a collagen gel (12), whereby enabling the assessment of the sensitivity of the normal tissue to a chemical or irradiation.

With regard to the prediction of the major and side effects of a pharmaceutical according to the invention, the use of a healthy human-derived normal regenerated tissue rather together with a normal regenerated tissue derived from a human having any pathological condition such as a life style-related disease (in a sense of a human having no cancer) may be of significance. In fact, it is preferable as a assessment system for the major and side effects on the cases of diabetes and the like.

For example, an inventive method described above can improve the true positive rate by overcoming a clinically disadvantageous aspect associated with a conventional collagen gel-employing histoculture drug response assay (HDRA) or CD-DST whose true positive rate is as low as about 60% or less. On the contrary to the HDRA or CD-DST which is not regarded to be a recognized custom-made therapy which allows a most effective drug to be selected and which is disappointed by most of clinical practitioners because of the fact that it can select an effective drug at a probability as low as about 50%, an inventive method limits the concentration of an exogenous growth factor in a culture medium to a low level and employs a normal tissue from an individual case, whereby enabling a simultaneous detection of the side effects on the normal tissue and the sensitivity of a cancer tissue coexisting with the normal tissue, thus realizing a so-called custom-made cancer therapy. The inventive method can be applied also to a method for producing a regenerated tissue or organ from a stem cell other than a TS without adding an excessive amount of a differentiation-inducing agent or an exogenous biological factor.

An inventive method is useful also as an in vitro assessment system for a gene therapy. While a two-dimensional culture system is employed for assessing the efficiency of a gene transduction and the like, it has a great limitation. An inventive regenerated tissue as an actual organ model is significant in terms of its 3-dimensional aspect.

In a tissue level investigation readily applicable to a cancer tissue 3-dimensional culture, a 1-3 mm-cube of a cancer tissue containing a tumor interstice is produced from an excised cancer tissue, mounted on a collagen gel in a multi-well culture dish, and allowed to stand preferably until the normal tissue is grown 3-dimensionally to 4 layers or more.

With regard to human organ-derived cells (tissue), those shown in Tables 3 and 4 are commercially available.

TABLE 3

|  | Manufacturer | Cell product number | Basal medium product number | Supplemented factor product number |
|---|---|---|---|---|
| Bronchial epithelium | Sanko Junyaku Co., Ltd (Clontics) | CC-2540 | CC-3119 | CC-4124 |
| Bronchiolar epithelium | Same as above | CC-2547 | CC-3119 | CC-4124 |
| Prostatic epithelium | Same as above | CC-2555 | CC-3165 | CC-4177 |
| Mammary gland epithelium | Same as above | CC-2551 | CC-3151 | CC-4136 |
| Pulmonary microvascular endothelium | Same as above | CC-2527 | CC-3156 | CC-4147 |
| Human hepatocyte | ASAHI TECHNOGLASS CORPORATION (Clontics) | CC-2591 | CC-3198 |  |
| Human neutrophile cell | Same as above | CC-2599 | CC-3209 | CC-4123 |
| Human proximal tubular epithelium | Same as above | CC-2553 | CC-3190 |  |
| Human skin-derived fibroblast | From Dr. ISHIZAKI | SuSa | Dulbecco MEM | 10% FBS |
| Human lung-derived fibroblast | ASAHI TECHNOGLASS CORPORATION (Clontics) | Normal 1 mg fibroblast |  |  |
|  |  | CC-2512 | CC-3131 | CC-4126 |
| Human umbilical venous endothelium | Same as above | HUVEC | CC-3156 | CC-4176 |
|  |  | CC-2517 | — |  |

Since a 3-dimensional culture of a normal tissue involves a significantly rapid proliferation of fibroblasts which are abundant in a submucosa and thus should be removed at a tissue level, it is cocultured to involve the following procedures.

1. A tissue mucosa taken upon surgery or biopsy is washed thoroughly with a phosphate buffered saline (Ca ion- and Mg ion-free) containing an antibiotic (containing 100 units/ml penicillin, 0.1 mg/ml, 0.25 μg/ml Fungizone).
2. The sample is treated for about 24 hours at 4.0° C. with a DME (containing FCS) containing a dispase (100 units/ml).
3. The epithelial layer and the submucosal layer are separated from each other mechanically.
4. Only the epithelial layer is treated for 30 minutes in a trypsin solution (containing 0.025% and 0.05% EDTA (only when trypsin is poorly effective).
5. The epithelial cells are separated by stirring with a magnetic stirrer.
6. The epithelial cells are collected by filtration through a nylon mesh filter.
7. Similarly, the vascular endothelial cells and the fibroblasts are separated from the submucosal layer for example by using a collagenase solution.
8. The cells thus obtained were sorted using monoclonal antibody labels to isolate respective fractions.
9. The supplemented factors such as a growth factor including serum are diluted to 1/10, or the culture is continued in a serum-free medium for 3 days, whereby suppressing the proliferation of the fibroblast.

TABLE 4

| Cell name | Cell product number |
|---|---|
| Bronchial epithelium (NHBE) | CCS-2540 |
| Pulmonary microvascular endothelium | CCS-2527 |
| Pulmonary fibroblast (NHLF) | CCS-2512 |
| Small airway (SAEC) | CCS-2547 |
| Prostatic epithelium (PrEC) | CCS-2555 |
| Mammary gland epithelium (HMEC) | CCS-2551 |
| Proximal tubular epithelial cell (RPTEC) | CCS-2553 |
| Mesangium cell (NHMC) | CCS-2559 |
| Neural progenitor cell (NHMP) | CCM-2599 |
| Human hepatocyte (Nheps) | CCS-2591 |

Any of these cells is co-cultured to be used as a sample in the invention. It is a matter of course that those listed above are not limiting.

Attached FIGS. 3, 4, 5 and 6 are the photographs obtained in the investigation of a 3-dimensional culture of a commercial human-derived normal tissue. These photographs correspond to those described below.

Figure 3:
FIG. 3 is a microscopic photograph showing the condition of a co-culture of normal pulmonary fibroblasts and vascular endothelial cells before the X-ray irradiation at 20Gy.

FIG. 3: The condition of a co-culture of normal pulmonary fibroblasts and vascular endothelial cells before the X-ray irradiation at 20Gy.

Figure 4:
FIG. 4 is a microscopic photograph showing the condition 24 hours after the transplantation of bronchial epithelial cells 24 hours after the irradiation described above.

FIG. 4: The condition 24 hours after the transplantation of tracheal epithelial cells 24 hours after the irradiation described above.

Figure 5:
FIG. 5 is a microscopic photograph showing the condition after 1 week.

FIG. 5: The condition after 1 week.

Figure 6:
FIG. 6 is a microscopic photograph showing the condition of the stratified structure having 4 layers or more although observed only partly.

FIG. 6: The condition of the stratified structure having 4 layers or more although observed only partly.

Based on the examples described above, the formation of a normal regenerated tissue of the invention was evident.

Figure 7:
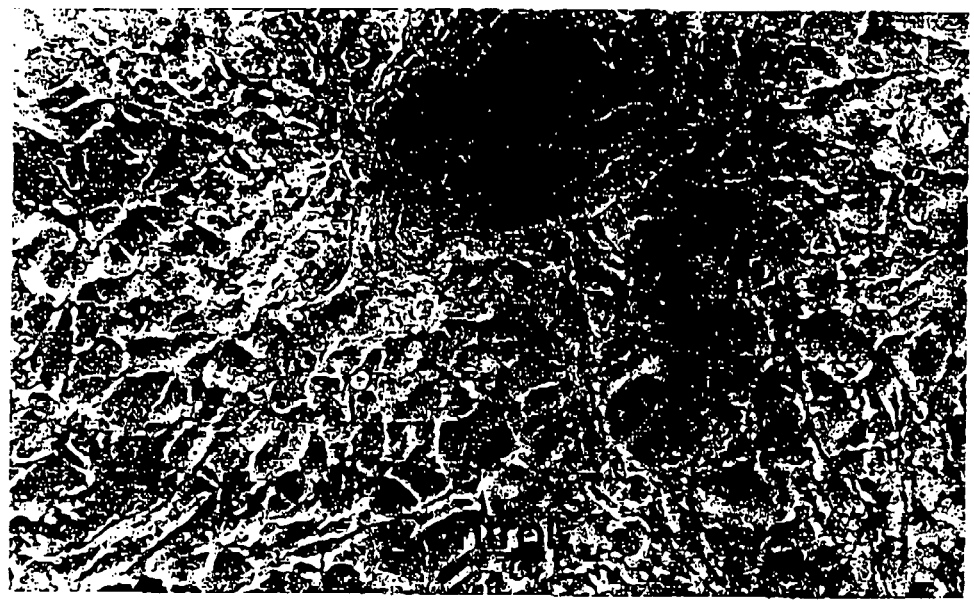
FIG. 7 is a microscopic photograph showing regenerated bronchial epithelial cells in a normal regenerated tissue by an inventive method.
Figure 8:
FIG. 8 is a microscopic photograph showing regenerated bronchial epithelial cells 3 days after the X-ray irradiation at 10Gy.
Figure 9:
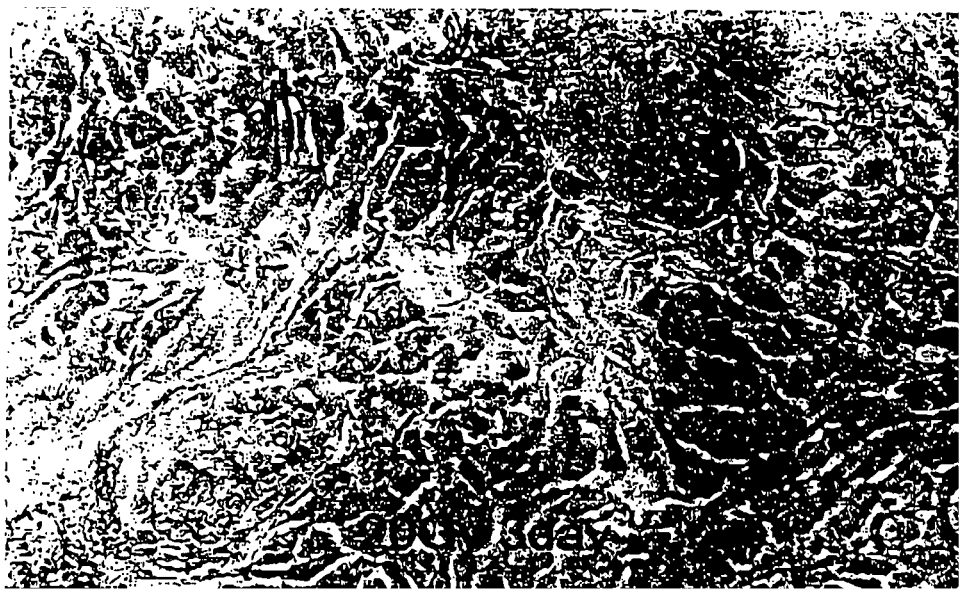
FIG. 9 is a microscopic photograph showing regenerated bronchial epithelial cells 3 days after the X-ray irradiation at 20Gy.
Figure 1:
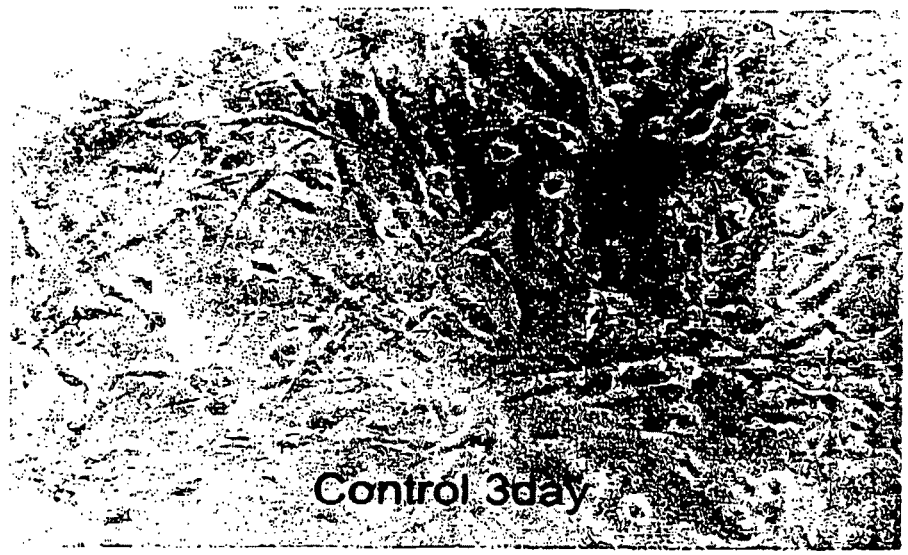
Figure 1:
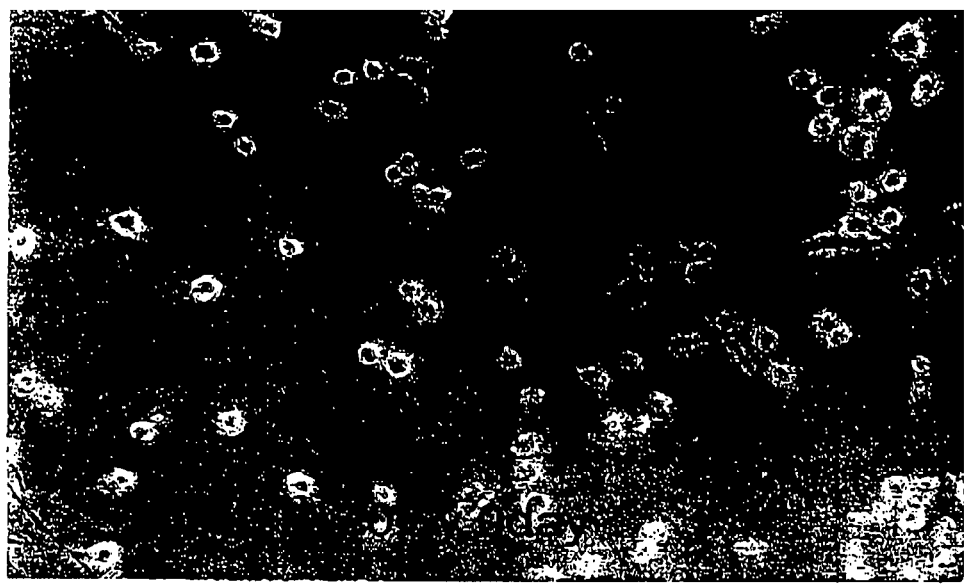
Figure 1:
Figure 1:

FIGS. 7, 8 and 9 are those described below.

FIG. 7: The regenerated bronchial epithelial cells in a normal regenerated tissue by an inventive method.

FIG. 8: The regenerated bronchial epithelial cells 3 days after the X-ray irradiation at 10Gy.

FIG. 9: The regenerated bronchial epithelial cells 3 days after the X-ray irradiation at 20Gy.

As evident from these photographs, it is possible to assess the sensitivity of a normal cell tissue to an X-ray.

FIGS. 10, 11, 12 and 13 are those described below.

FIG. 10: The condition of regenerated bronchial epithelial cell layer formed by an inventive method which had been supplemented with a collagen gel and then transplanted with human pulmonary cancer-derived AOI cells after three days.

FIG. 11: The condition immediately after the X-ray irradiation at 20GY 3 hours after the transplantation similar to that in FIG. 10.

FIG. 12: The condition 3 days after the irradiation in the case shown in FIG. 11.

FIG. 13: The condition after the X-ray irradiation at 10Gy in the case shown in FIG. 12.

As evident from FIGS. 10 to 12, it is possible to assess the sensitivity of pulmonary cancer cells to an X-ray and the anti-cancer effect of the X-ray irradiation. A carcinostatic agent may be assessed similarly.

Embodiment 2

Similarly to those described above, various human organ-derived regenerated tissues were formed and subjected to the cancer therapy sensitivity test.

1. Preparation of Mucosal Sheet 1.1 Preparation of SuSa (Feeder Layer)

As a feeder layer, SuSa (human fibroblasts) was employed. The culture medium employed was a 10% foetal calf serum (Sigma chemical Co., hereinafter referred to as FCS)-supplemented Dulbecco's Modified Eagle Medium (Sigma chemical Co., hereinafter referred to as DEME). A 24-well plate was inoculated at $5 \times 10^4$ cells/cm$^2$ per well, and irradiated with 20Gy of an X-ray after 24 hours.

1.2 Preparation of Epithelial Cells

The epithelial cells employed were renal proximal tubular epithelial cells (RPTEC), mesangium cells (NHMC), prostatic epithelial cells (PrEc), neural progenitor cells (NHMP), human hepatocytes (NHeps) and mammary gland epithelial cells (HMEC) (all from Clontech). The culture medium formulations employed were a renal epithelial cell basal medium (Clontech, REBM) containing 6.51 ng/ml *TRIIODESILONINE*, 0.5 µg/ml epinephrin, 1 µg/ml GA-1000, 10 µg/ml transferrin, 5 µg/ml insulin, 0.5 µg/ml hydrocortisone, a renal epithelial cell basal medium (Clontech, REBM), 0.01 µg/ml hEGF, 0.5% of FBS for the RPTEC, a mesangial cell basal medium (Clontech, MsBM) containing 1 µg/ml GA-1000, 5% FBS for the NHMC, a prostate epithelial cell basal medium (Clontech, RrEBM) containing 13 µg/ml BPE, 5 µg/ml insulin, 1 µg/ml GA-1000, 0.1 ng/ml retinic acid, 10 µg/ml transferrin, 6.51 ng/ml *TRIIODESILONINE*, 0.5 µg/ml hydrocortisone, 0.5 µg/ml epinephrin and 0.01 µg/ml hEGF for the PrEC, a neural progenitor basal medium (Clontech, NPBM) containing 0.01 µg/ml hEGF-8, 0.01 µg/ml hEGF, 0.8% of NSF and 1 µg/ml 1GA-1000 for the NHMP, a hepatocyte basal medium (Clontech, HBM) containing 0.5 µg/ml hydrocortisone, 0.01 µg/ml hEGF, BSA, ascorbic acid, 10 µg/ml transferrin, 5 µg/ml insulin and 1 µg/ml GA-1000 for the NHEPS, and a mammary epithelial basal medium (Clontech, MEBM) containing 5 µg/ml insulin, 1 µg/ml GA-1000, 0.01 µg/ml hEGF, 13 µg/ml BPE and 0.5 µg/ml hydrocortisone for the HMEC. A collagen dish (IWAKI) was used for the incubation under 5% $CO_2$ at 37° C., and each strain was inoculated upon 80% to 90% confluent at $5 \times 10^3$ cell/cm$^2$ per well on the feeder layer described above which had previously been provided using 6 24-well plates per strain.

1.3 Regenerated Sheet Incubation

A mucosal sheet incubation was conducted using a DMEM (−). The culture medium was supplemented with a 1% Anti-B, 10% fetal bovine serum (JRH BIOSCIENCES, hereinafter referred to as FBS), 5 µg/ml insulin, 5 µg/ml transferrin, $2 \times 10^{-5}$ M *TRIIODESILONINE*, $1 \times 10^{-9}$ M cholera toxin, 0.5 µg/ml hydrocortisone, 10 ng/ml human epithelium growth factor (EGF: Takara), 1000/ml penicillin G (MEIJI SEIKA), 1 mg/ml kanamycin (Sigma, St. Louis, Mo., USA), and 2.5 µg/ml Fungizone (Gibco, Grand Iskl, and NY, USA). The incubation was conducted at 37° C. in a 10% $CO_2$ incubator with replacing the culture medium every two days. After removing the culture medium after 10 days, a collagen gel which was a 8:1:1 mixture of a gel matrix type A gel, 10×MEM (NaOH-free) and a 0.05N—NaOH (NITTA GELATINE) containing 2.2% NaOH and 200 mM HEPES was applied in a volume of 0.5 ml per well in the 24-well plate. After the incubation for 20 days, the plates are divided to obtain duplicate samples for an MTT assay, and the RPTEC and the NHMC were inoculated with ACHN-L4, the PrEC with DU145, the NHMP with A7, the Nhep with Alex and the HMEC with MDA-MB-453, all at $5 \times 10^4$/cm$^2$. 4 Hours after the inoculation, a CDDP was added and an X-ray irradiation was performed at 0Gy (control) and 0Gy after 24 hours. 72 Hours after the irradiation, the MTT assay sampling was performed.

2. MTT Assay

After the treatment with the CDDP, the culture medium was removed after 72 hours, and the collagen gel was cut into about 3 mm-cube pieces, combined with a 0.2% collagenase, dissolved with shaking at 37° C., centrifuged at 1000 rpm for 5 minutes to separate the cells, which were then resuspended in the culture medium, which were then returned to a 24-well plate. 0.5 mg/ml MTT labeling reagent (Roche Diagnostics, hereinafter designated as Roche) was added, and the plate was incubated in a 10% $CO_2$ incubator at 37° C. for 4 hours, and a solubilization solution (Roche) in a volume equal to that of the culture medium was added and incubated in a 10% $CO_2$ incubator at 37° C. for 24 hours. From each well, 200 µl aliquots were transferred to a 96-well plate, which was examined for the absorbance at the wavelength of 600 nm using a multiplate reader to obtain a measured value as an average of 3 wells.

3. Types of Tissues Derived from Organs Capable of being Regenerated

Any of the cells employed here, namely, the renal proximal tubular epithelial cells (RPTEC: FIG. 14), mesangium cells (NHMC: FIG. 15), prostatic epithelial cells (PrEc: FIG. 16), neural progenitor cells (NHMP: FIG. 17), human hepatocytes (Nheps: FIG. 18) and mammary gland epithelial cells (HMEC: FIG. 19), became a stratified structure within 10 days after initiation of the culture. Most of them became a 4-stratified structure within 3 weeks. Also since the stratified structure had already been observed after 5 days which was earlier than the time when the gel was mounted for example on the mesangium cells (NHMC), it was verified that the collagen gel was not essential for the regeneration.

4. Results of Cancer Therapy Sensitivity Test

The results of the sensitivity test by the MTT assay are shown in FIGS. 20 to 23. The designation gel+cancer in the figures corresponds to a conventional HDRA method. An inventive sensitivity test is represented by an epithelium+gel+cancer, while an epithelium+gel represents the sensitivity of a normal tissue. Since the cancer cells were not separated exclusively, the MTT assay of the epithelium+ gel+cancer gave the results as a total of the cancer tissue plus the normal tissue which was irradiated at 20Gy and became a feeder layer.

Figure 20:
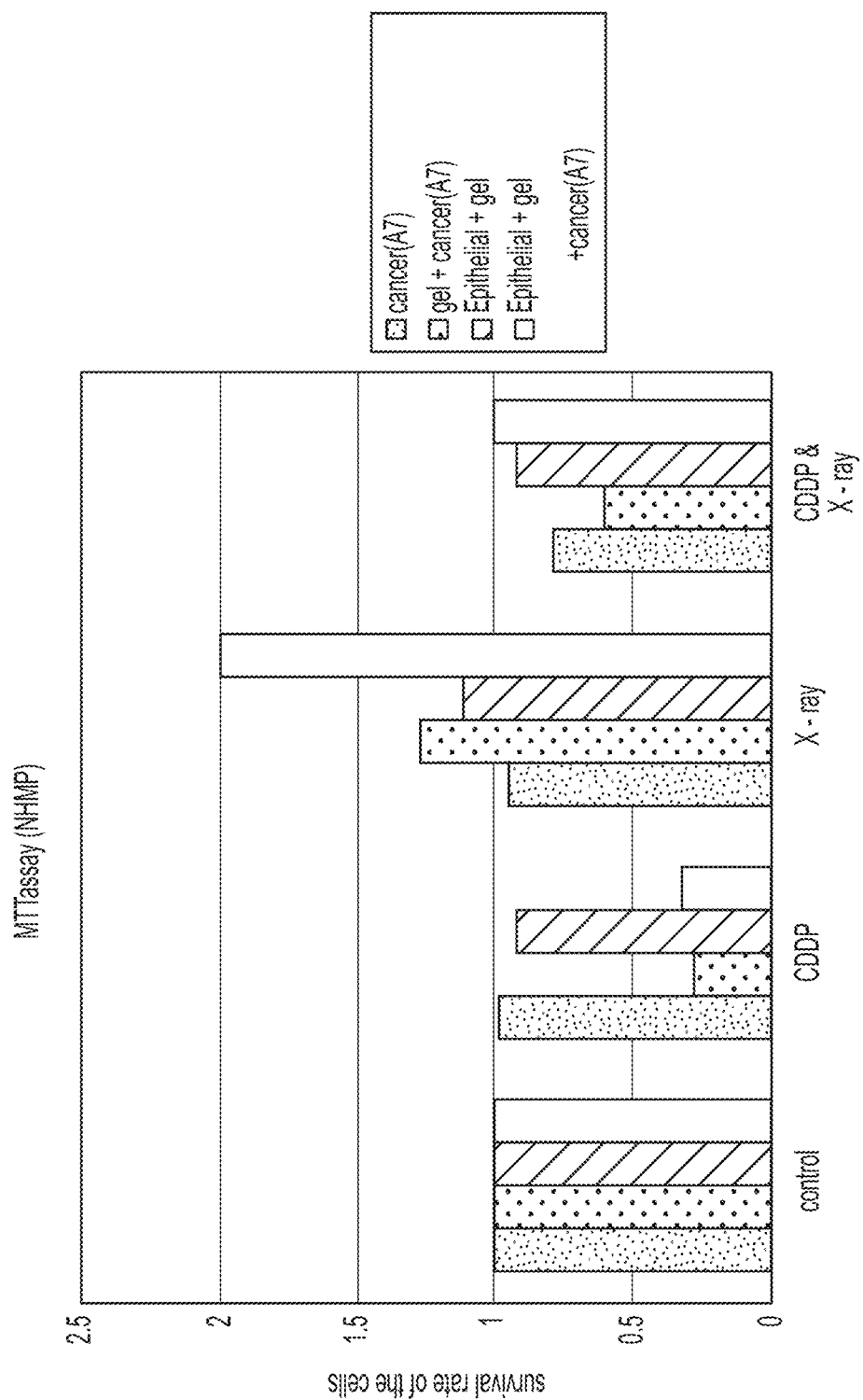
FIGS. 20, 21, 22 and 23 show the results of the cancer therapy sensitivity test by an MTT assay of the above-mentioned NHMP, PrEC, NHMC and PRTEC, respectively.
Figure 21:
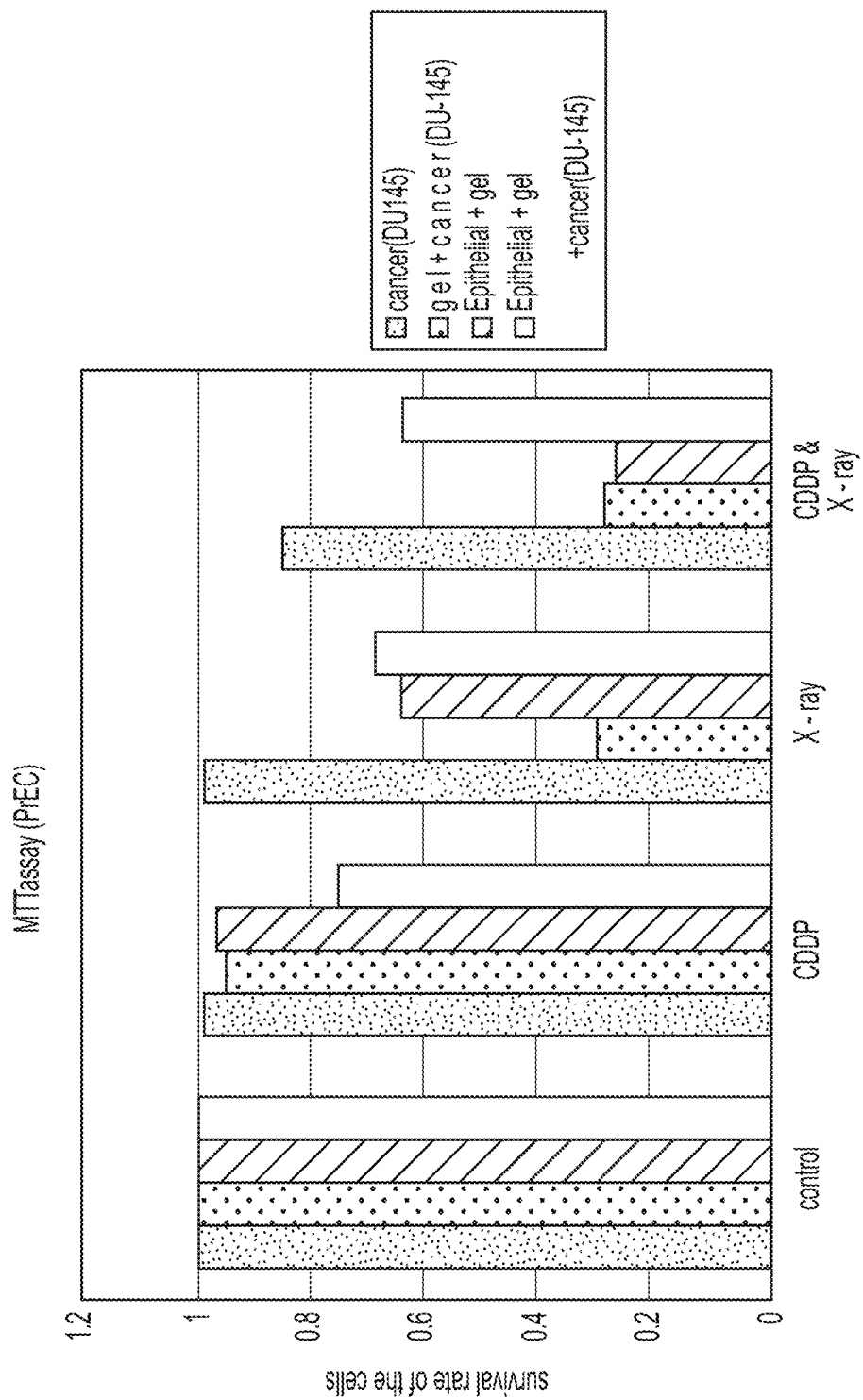
Figure 22:
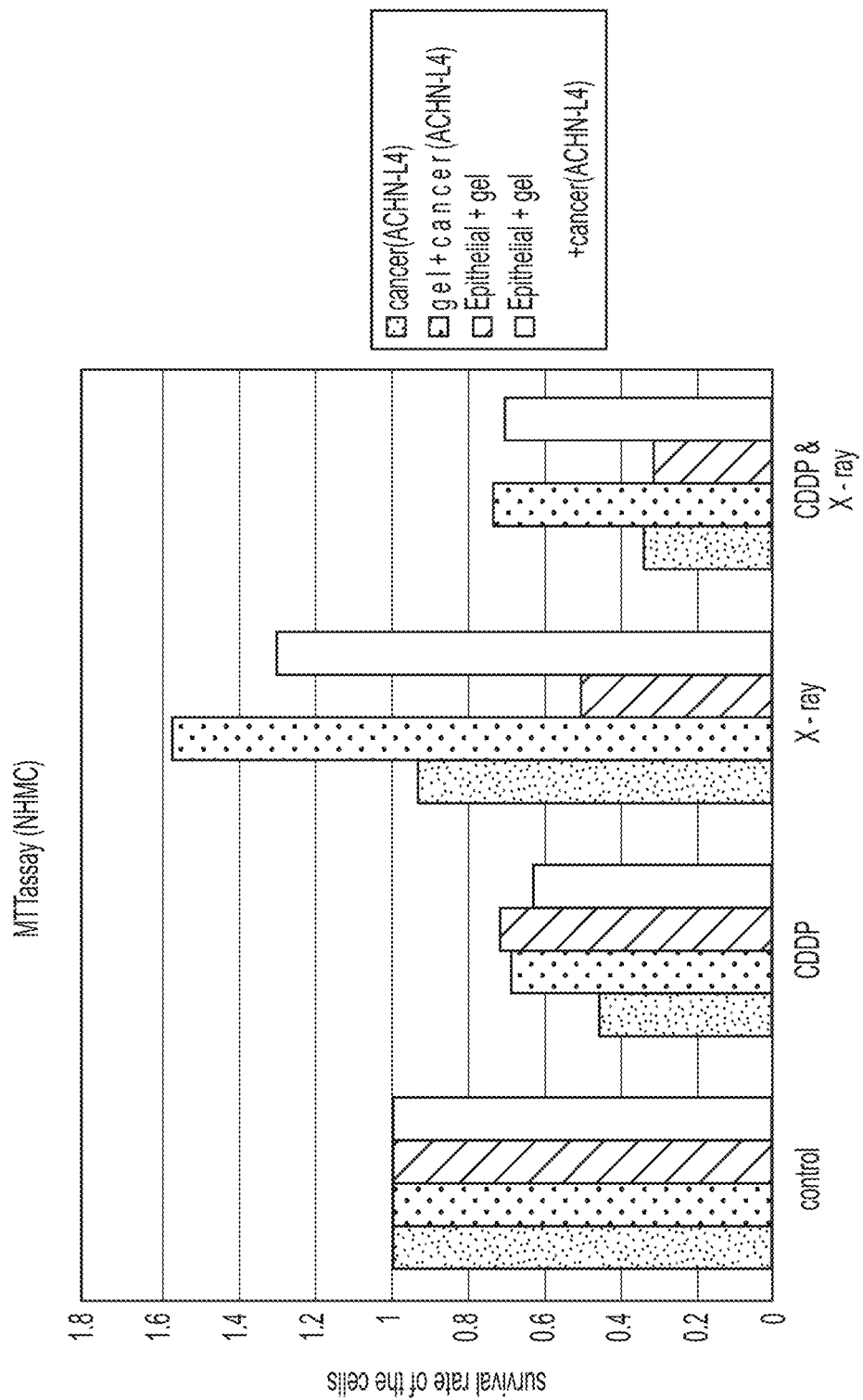
Figure 23:
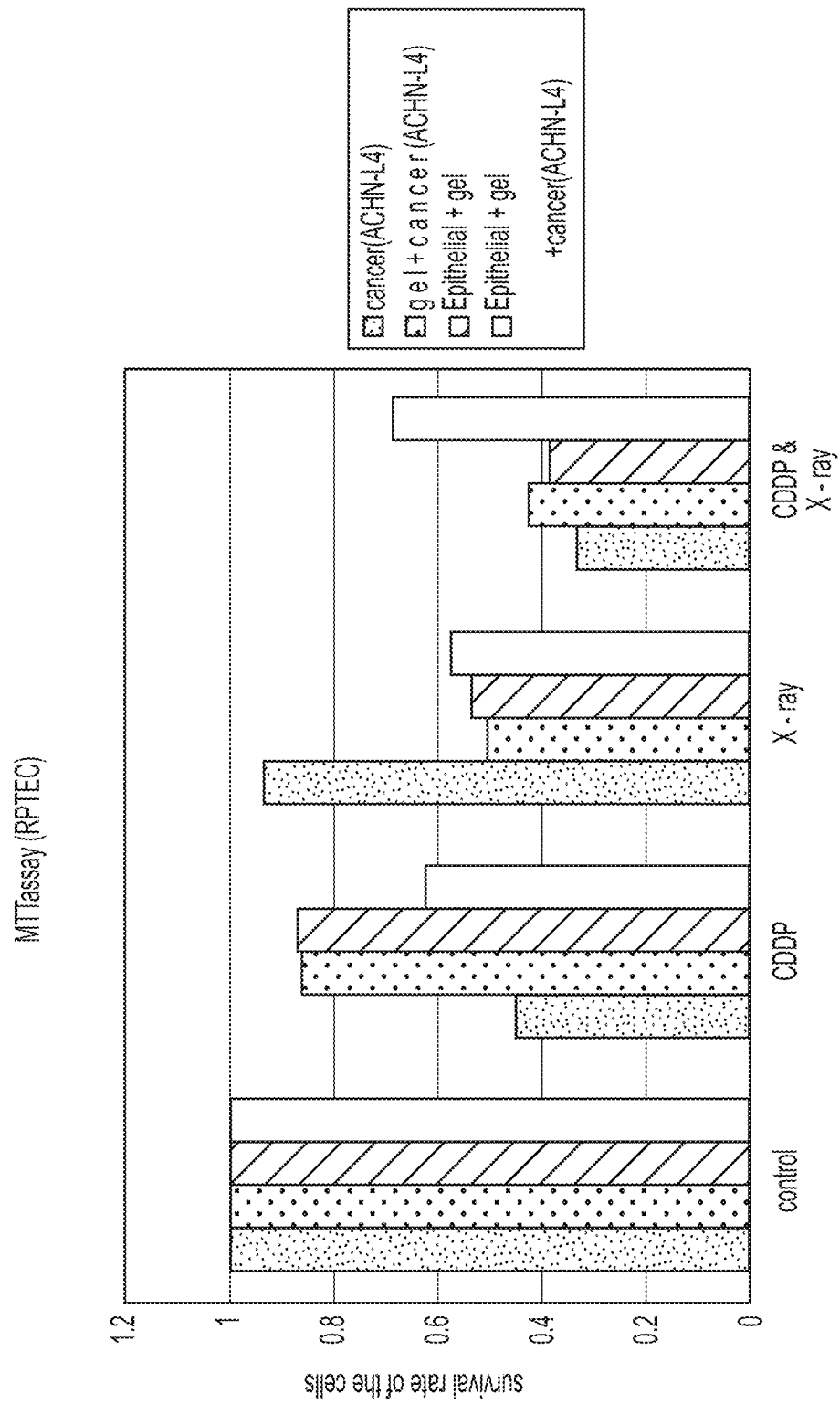
Figure 24:
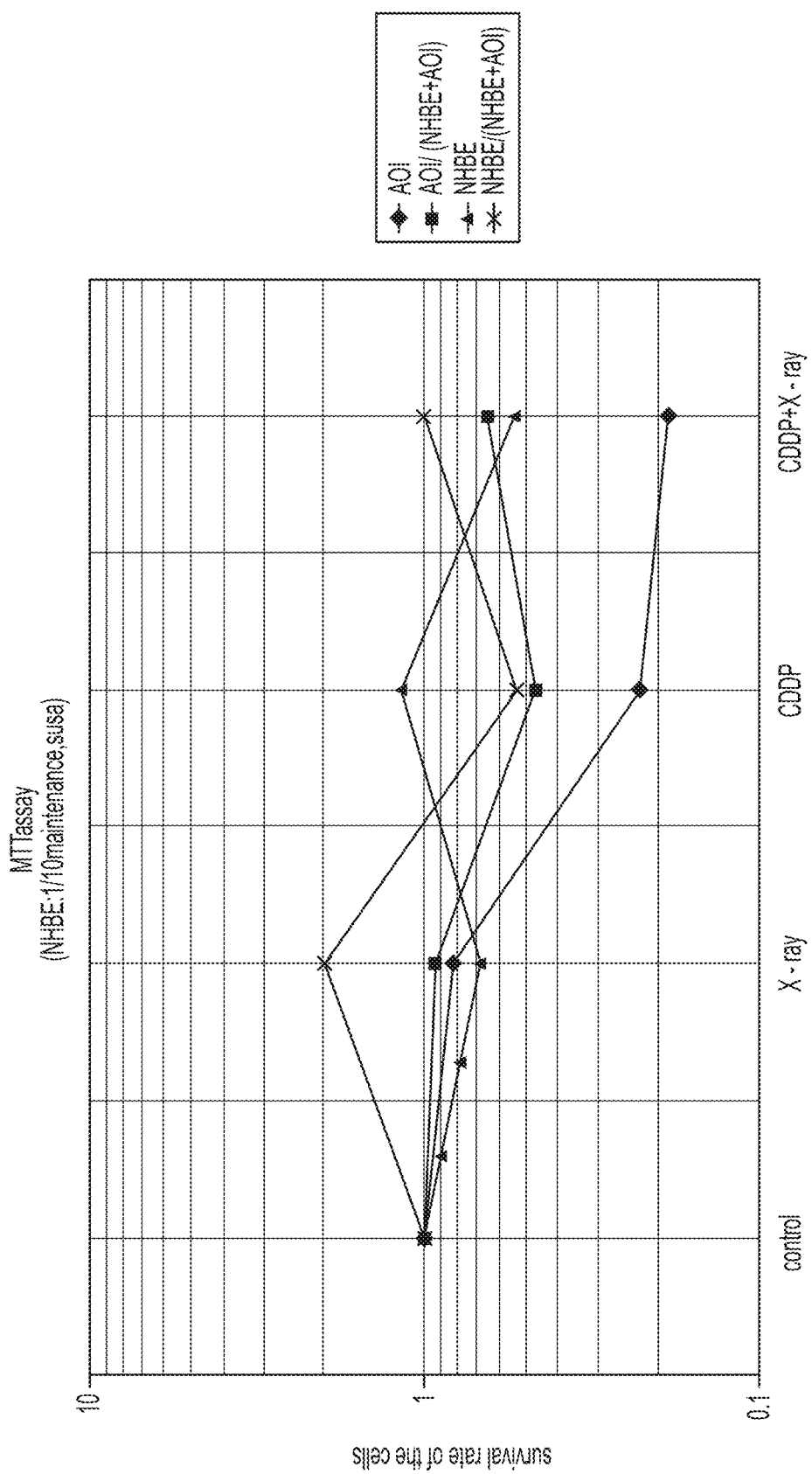
FIGS. 24, 25, 26, 27, 28 and 29 show the results of the cancer therapy sensitivity test by an MTT assay of an NHBE in a stratified structure in Embodiment 3 using SuSa (derived from skin) as a feeder layer.
Figure 25:
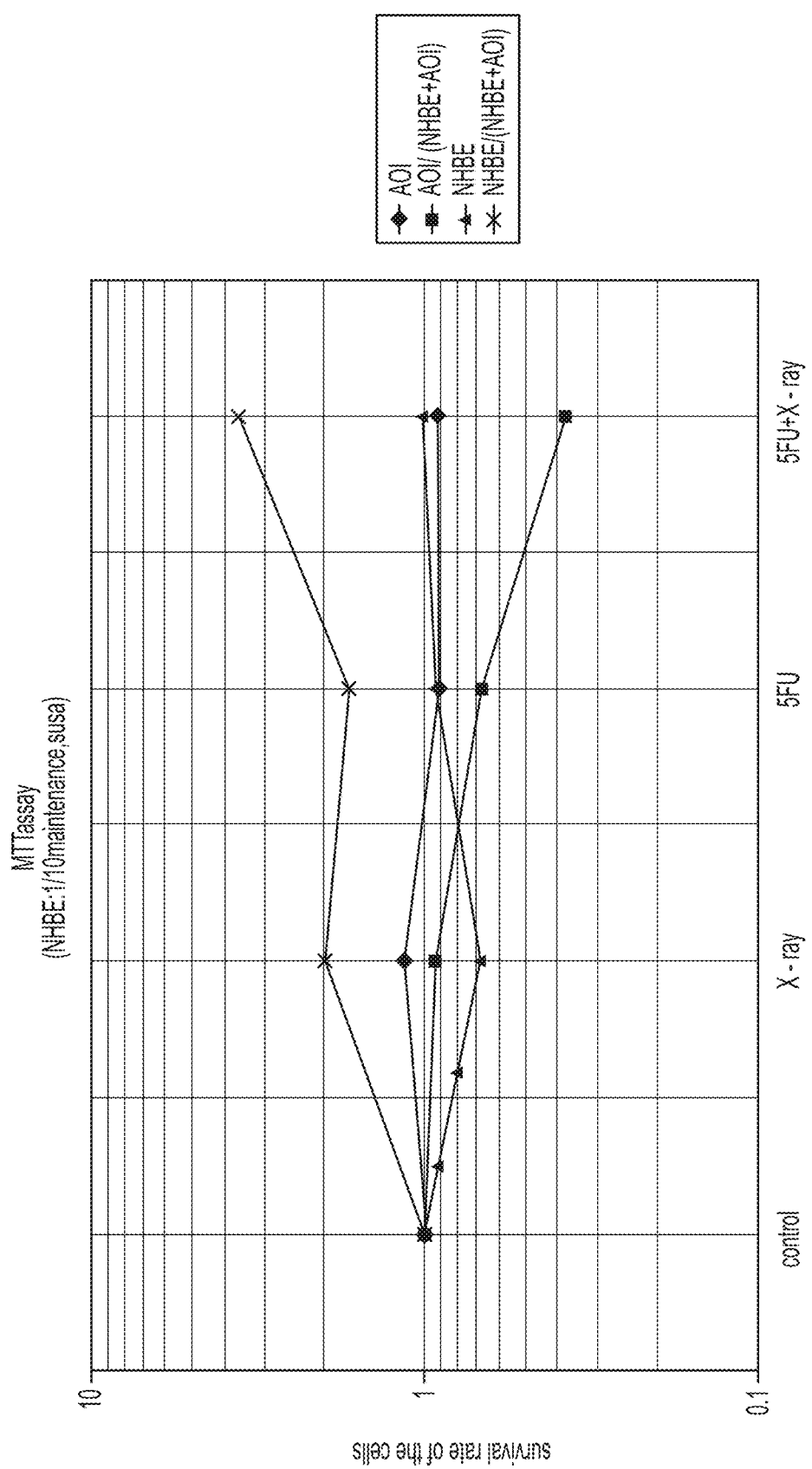
Figure 26:
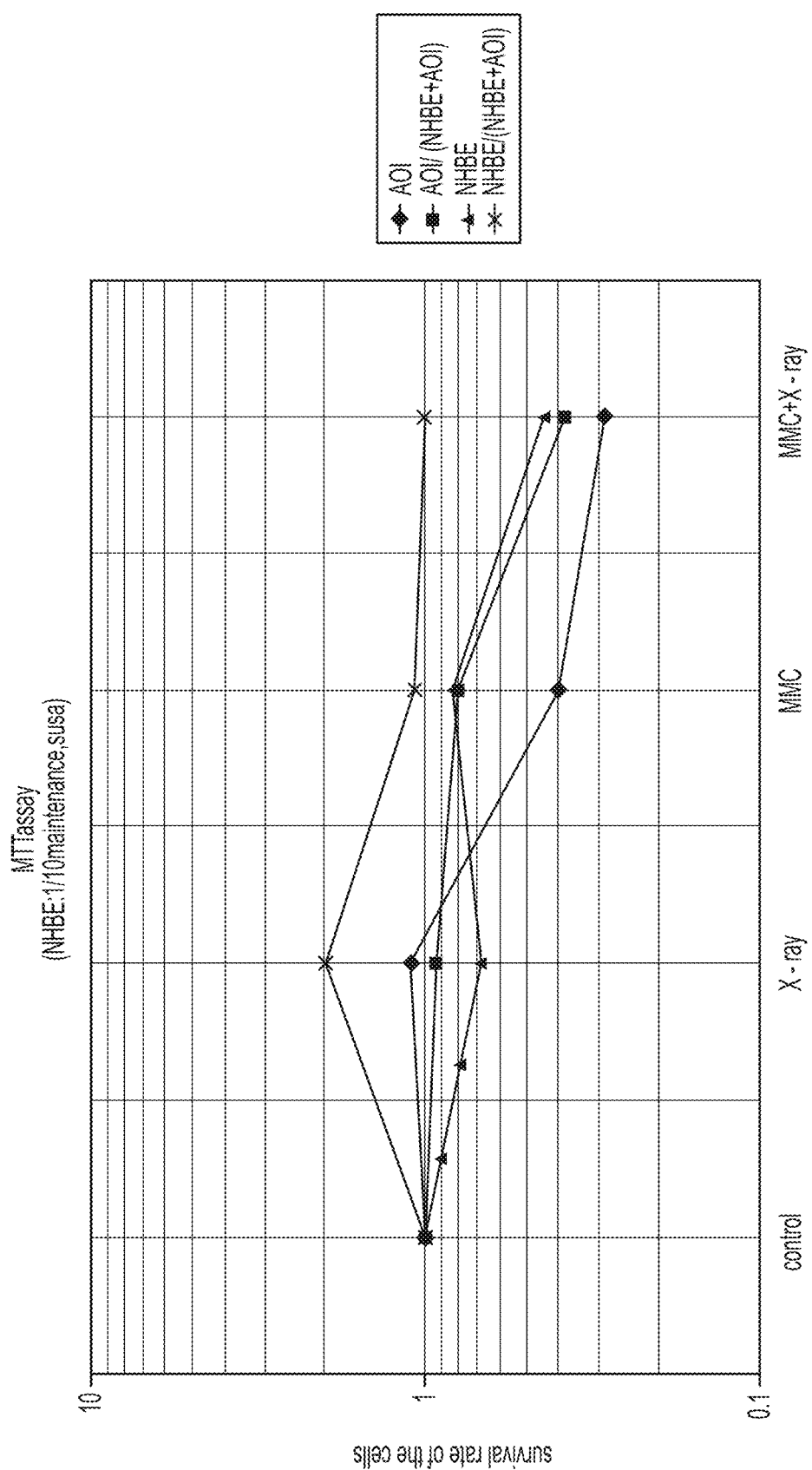
Figure 27:
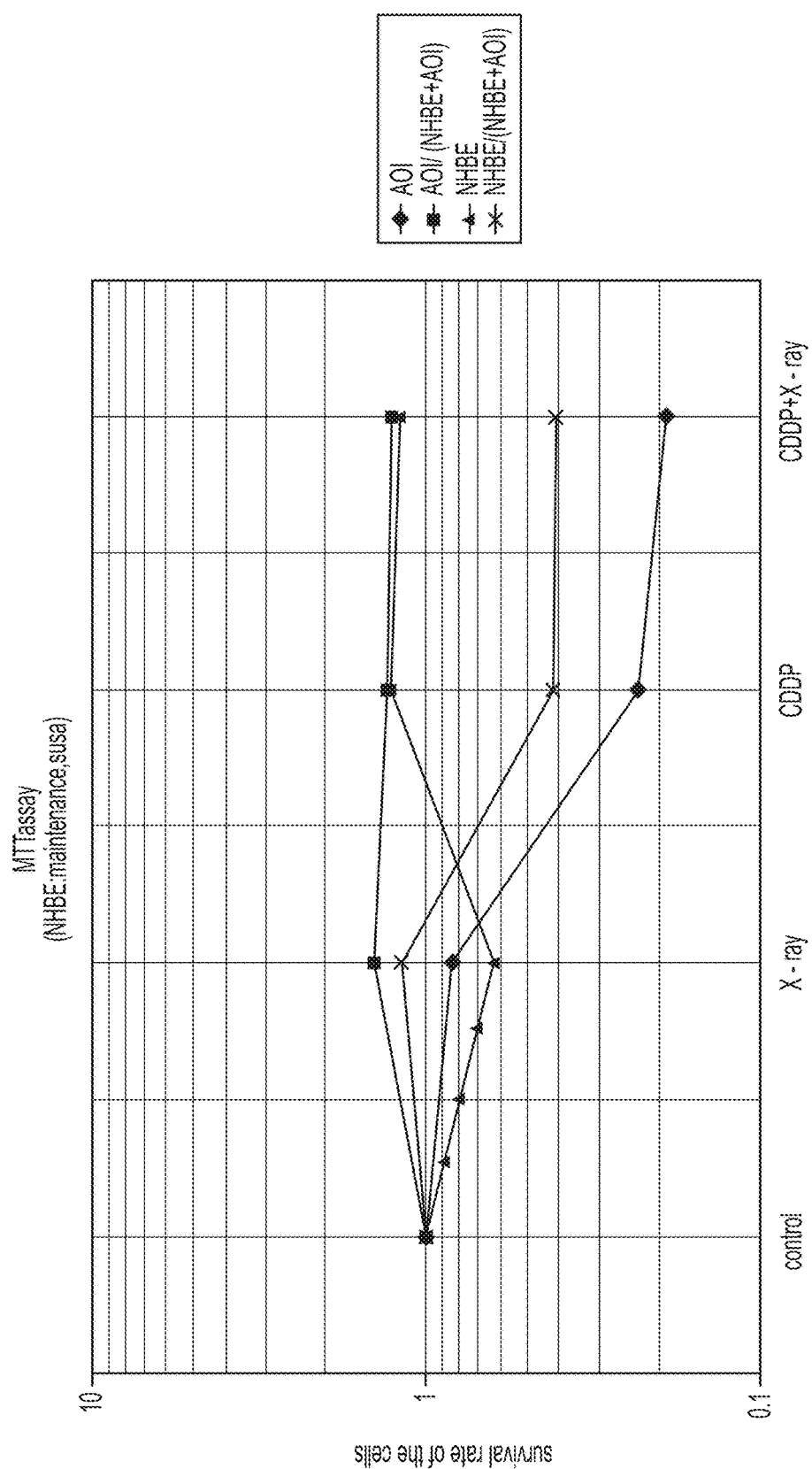
Figure 28:
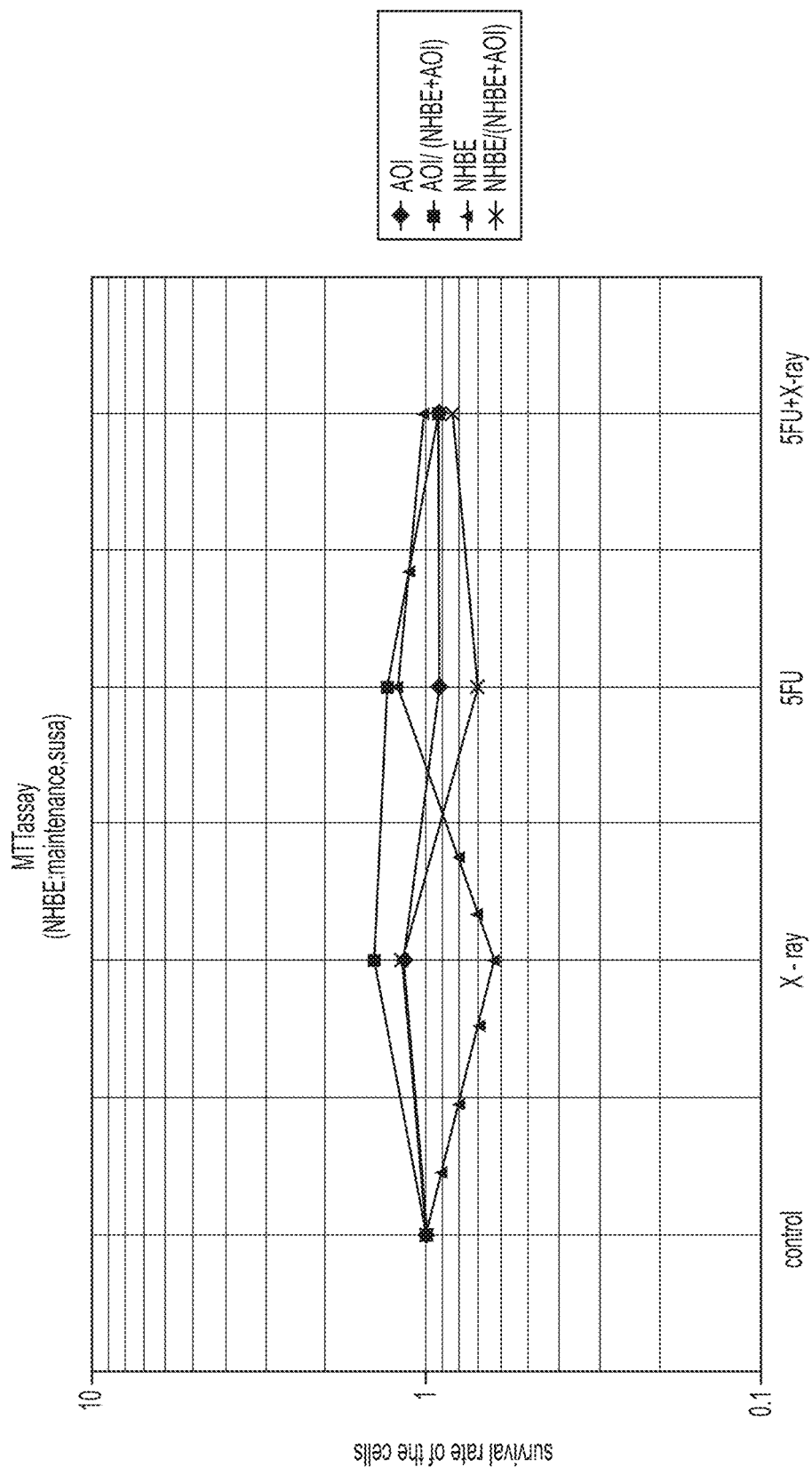
Figure 29:
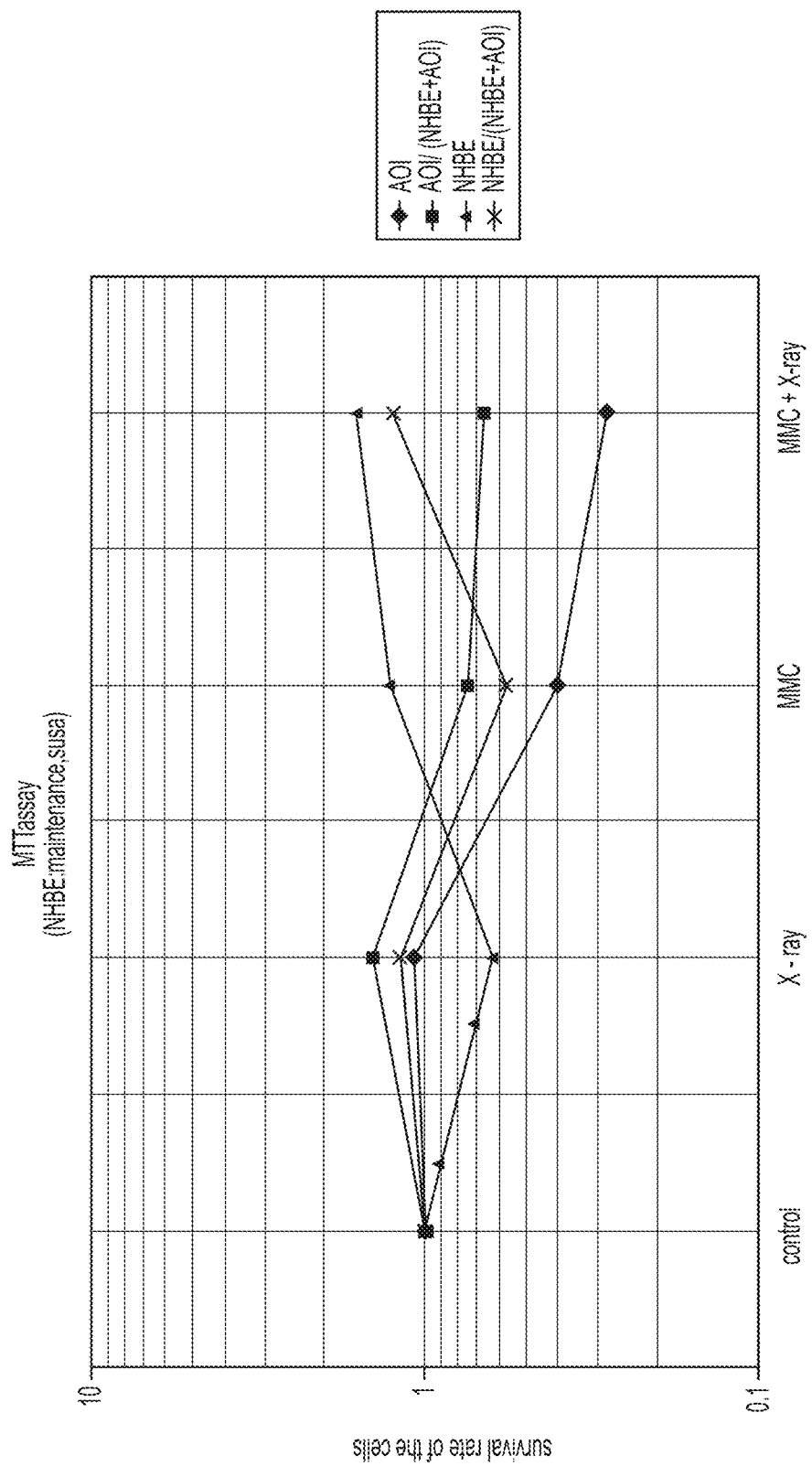
Figure 30:
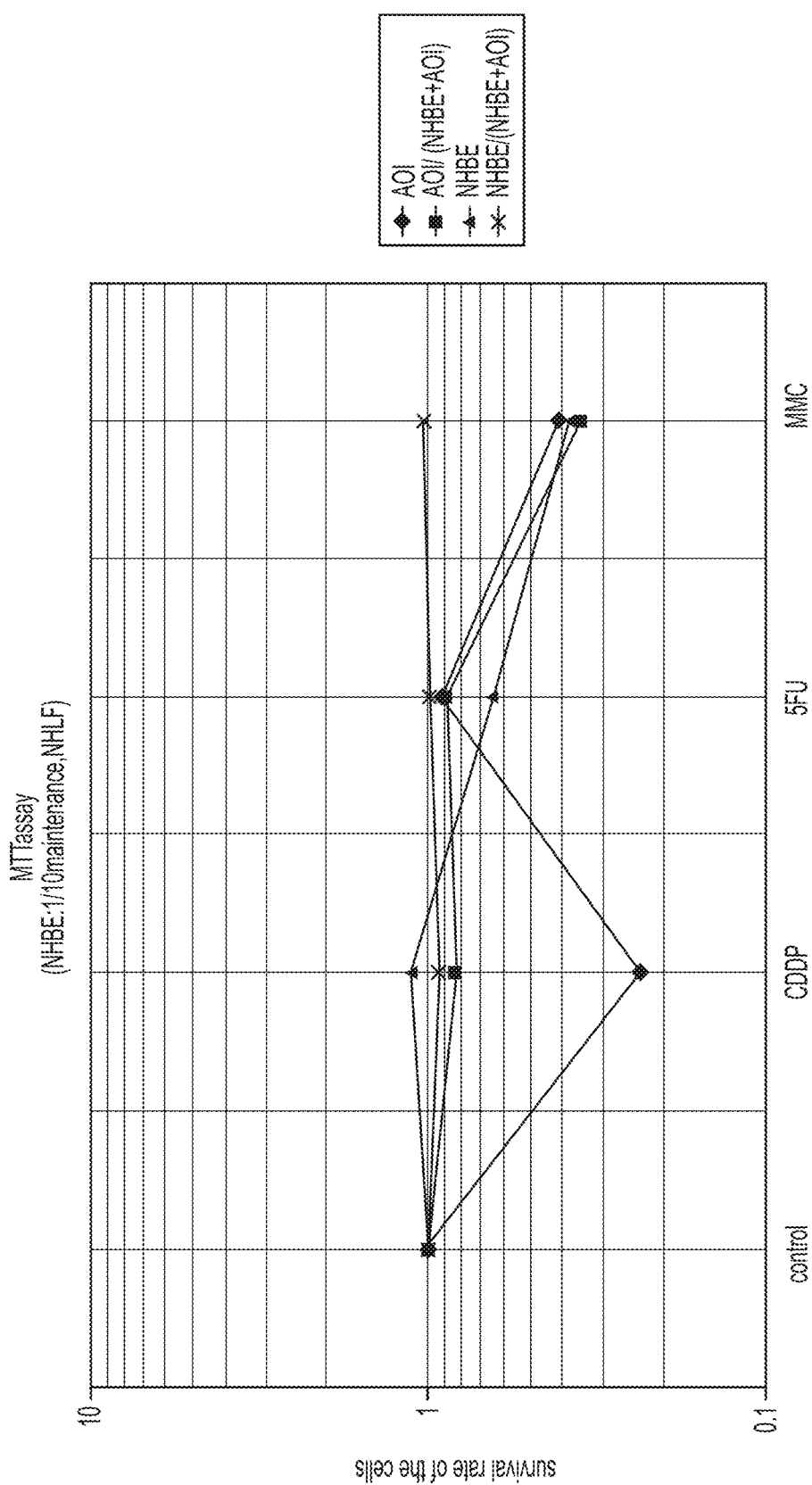
FIGS. 30 and 31 show the results of the cancer therapy sensitivity test by an MTT assay of NHBE in a stratified structure using NHLF (derived from lung) as a feeder layer.
Figure 31:
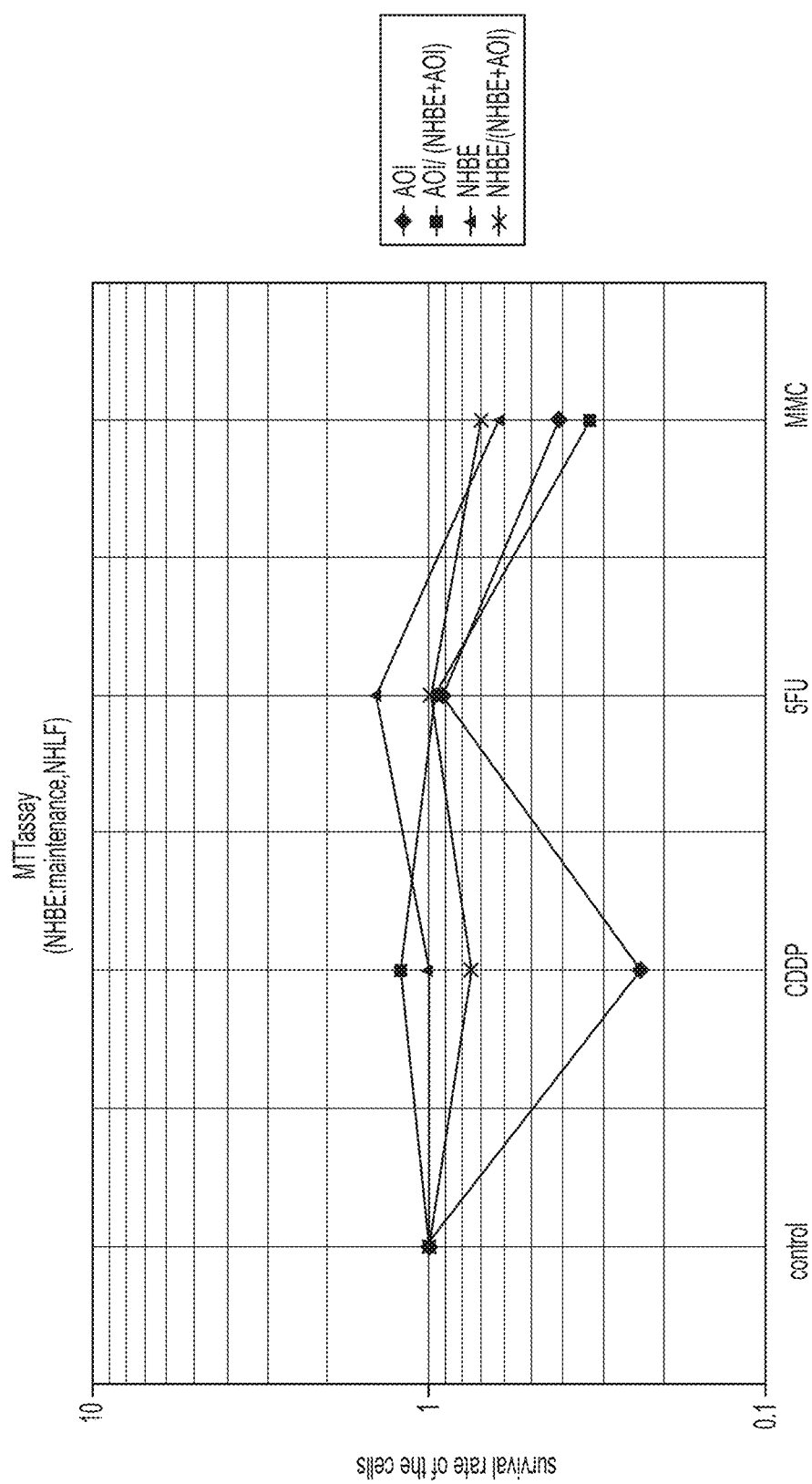
Figure 32:
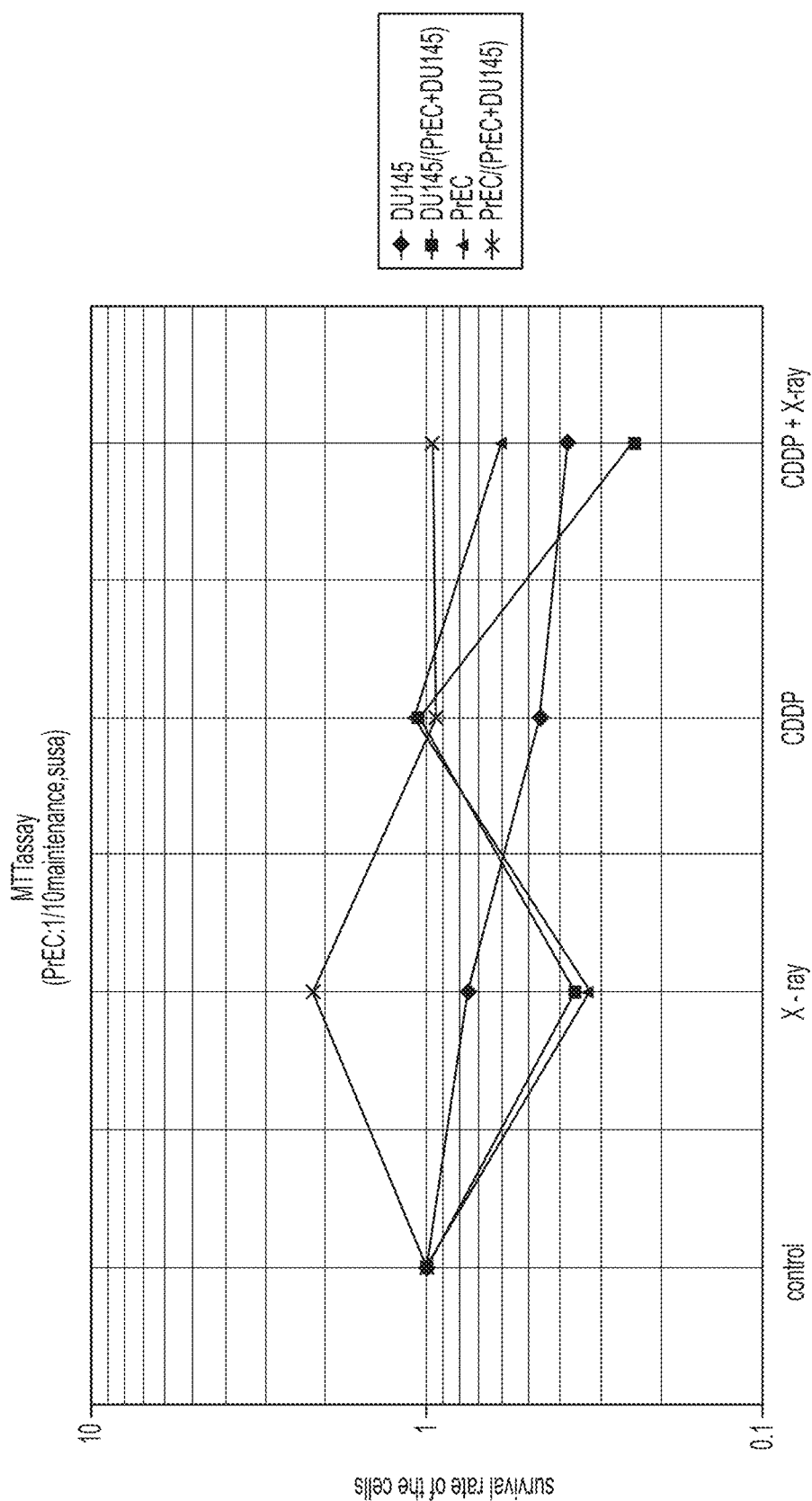
FIGS. 32, 33 and 34 show the results of the cancer therapy sensitivity test by an MTT assay of PrEc in a stratified structure using SuSa (derived from skin) as a feeder layer.
Figure 33:
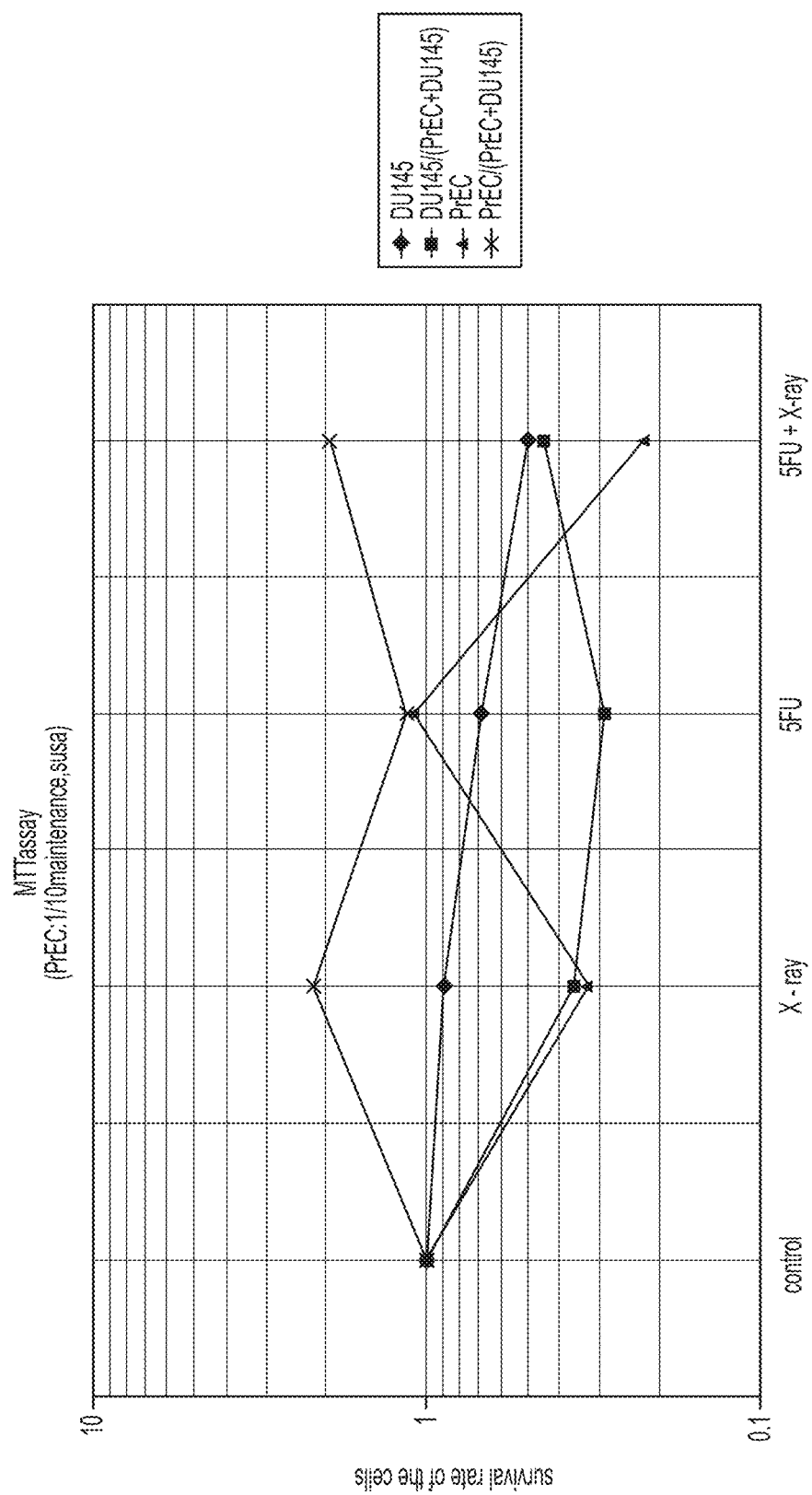
Figure 34:
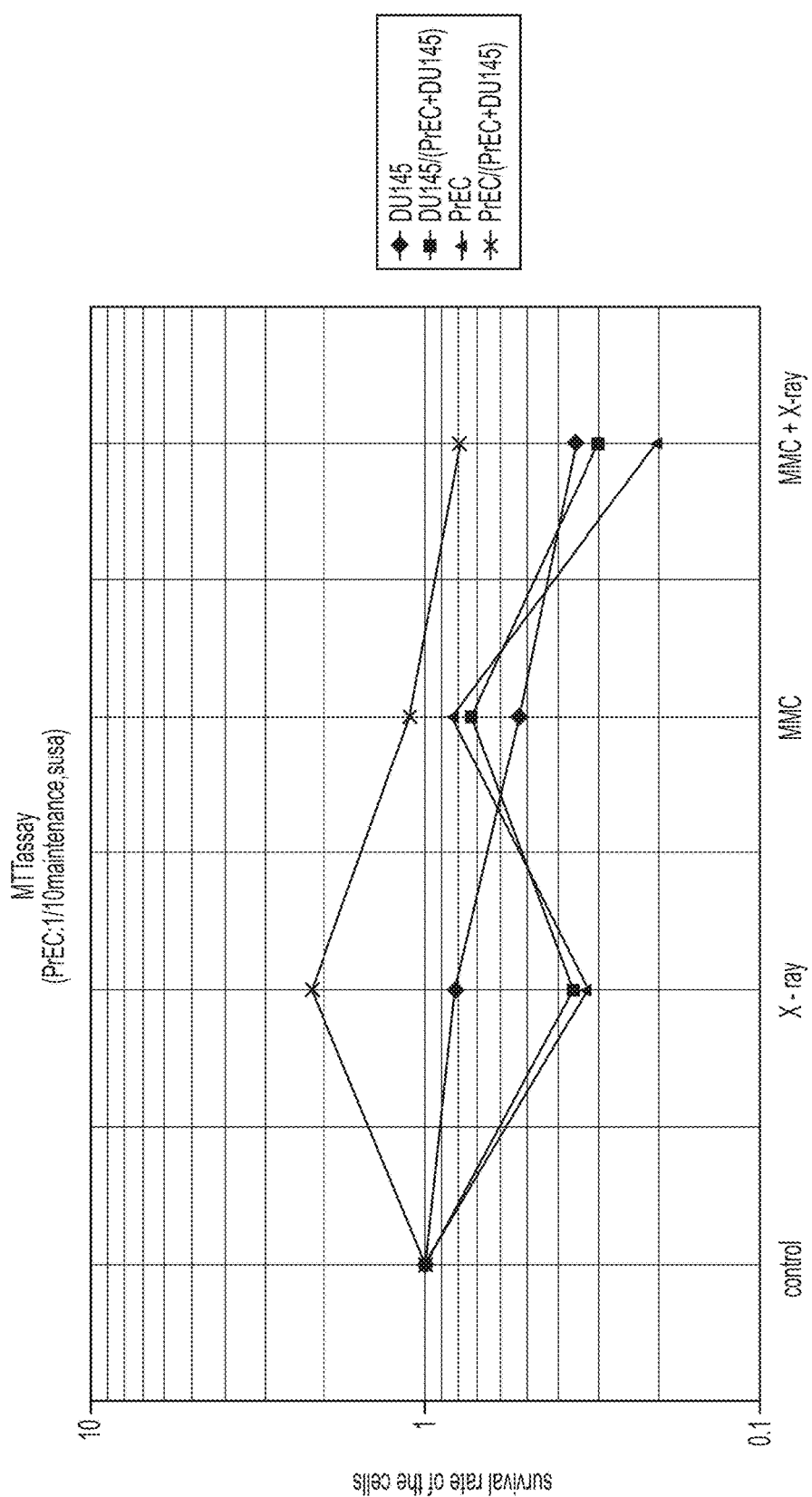

In the cancer cells, a nude mouse-transplanted tumor and a clinically radiochemotheapy-resistant glioblastoma multiform derived A7 cells exhibited a more resistance in the MTT assay than in the HDRA method (FIG. 20). The hepatoma cells Alex in the MTT assay exhibited no significant difference from the HDRA method, but the combination with cisplatin exhibited the difference in the effect. While the prostatic cancer cells DU145 in the MTT assay exhibited an extremely high sensitivity to the irradiation in the HDRA method, but it has been recognized clinically to be less sensitive in an experiment of a nude mouse-transplanted tumor test, resulting in a rather closer sensitivity observed in the inventive method. Finally, it was revealed clinically that also in the nude mouse-transplanted tumor the radio-resistant renal cancer ACHN-L4 exhibited a irradiation sensitivity which differed between the mesangium cells NHMC- and the renal proximal tubular epithelial cells RPTEC-derived supporting tissues (FIGS. 22 and 23). Thus, these results are very interesting because they suggested that the sensitivity of identical cancer cells differed between the different supporting tissues. The cisplatin sensitivity indicated that the inventive sensitivity test gave the results which were closer to those observed in the nude mouse-transplanted tumor. When the sensitivities of various cancer cells observed in the novel sensitivity test are compared in the MTT assay, the results observed in the ACHN-L4 cells which are highly sensitive to cisplatin showed an agreement.

Embodiment 3

The cancer therapy sensitivity test was conducted in comparison with a conventional two-dimensional culture MTT assay system.

The results are shown in FIGS. 24 to 34. In these figures, a column of the cancer name (e.g: AOI) corresponds to the sensitivity of the cancer cells in the two-dimensional culture. The second column (e.g.: AOI/(NHBE+AOI) corresponds to the sensitivity observed after treating the cancer tissue which had been subjected to a 3-dimensional culture on regenerated normal tissue followed by conducting the MMT assay using only the cancer cells. The third column (e.g.: NHBE/(NHBE+AOI)) corresponds to the sensitivity observed after culturing only normal cells followed by co-culturing with the cancer tissue followed by removing the cancer tissue to test only the 3-dimensionally regenerated normal tissue.

Also in these figures, the brackets the MTT assay correspond, from the left, the normal epithelial cell name employed (this time a bronchial epithelium (NHBE) or prostatic epithelium (PrEC)), the culture medium (1/10-fold or 1-fold), the fibroblast name employed as a feeder layer (human skin-derived (SUSA) or lung-derived (NHLF)). Control corresponds to the results of the MTT assay in a non-treatment group, X-ray to the results of the MTT assay 72 hours after a single irradiation at 10Gy, 5FU to the MTT assay data after the treatment with 5FU for 72 hours at 10 μg/ml, 5FU-X-ray to the MTT assay data after the treatment with 5FU for 3 hours at 10 μg/ml followed by the treatment with 5FU for 72 hours concomitantly with a 10Gy irradiation. The drug treatments with all of three drugs employed here were conducted at 10 μg/ml for 72 hours.

Typically, the drug treatments were conducted while comparing three anti-cancer agents (CDDP, MMC, 5FU).

<A> Results with Skin-Derived Fibroblasts (SUSA) as Feeder Layer

1. As a result, the 3-dimensional normal tissue coexisting with the cancer tissue was revealed to be rather more resistant to the irradiation, MMC alone or MMC+X-ray when compared with the normal tissue alone, possibly because for example of the level of the growth factor was 1/10 in the 1/10-level medium. It was also revealed that, when compared with the 2-dimensionally cultured AOI lung cancer cells, the 3-dimensional AOI cancer tissue coexisting with the normal tissue was more resistant to the MMC alone or MMC+X-ray.

2. The 3-dimensionally growing normal tissue was rather more resistant to the mitomycin MMC alone or MMC+X-ray, possibly because of the presence of an excessive amount of the growth factor in the 1-fold level culture medium. The 3-dimensional AOI cancer tissue was rather more resistant than the two-dimensionally cultured AOI cancer cells, possibly because of the presence of the signals such as a growth factor from the normal bronchial epithelium which was co-cultured and subjected further to a 10Gy irradiation.

3. The tendency described above was observed also with the anti-cancer agent cisplatin. Especially in the 3-dimensionally cultured AOI cancer cells, the degree of acquiring the resistance was influenced more potently by the level (of the growth factor) in the culture medium when compared with the two-dimensionally cultured AOI cancer cells. The tests with the irradiation or 5FU treatment in the 1/10-fold culture medium rather suggested that the tendency of the promotion of the growth of the regenerated normal bronchial epithelial tissue after removing the AOI cancer tissue which had been co-cultured. Also with the normal tissue alone, it was suggested that the frequency of the side effects was low. In the 1-fold culture medium, the proliferation was rather promoted by either of the irradiation or the treatment with 5FU alone possibly because of the presence of the added growth factor, but such a promoting effect disappeared when the both was given concomitantly. The side effects on the normal tissue was suggested to be exerted rather potently when the added growth factor level was high.

4. In the regenerated prostatic tissue in the 1/10-fold culture medium, the regenerated normal prostatic tissue after the removal of the prostatic cancer-derived DU-145 cancer cells irradiated at 10Gy exhibited a rather promoted proliferation. This cancer cells were revealed to be highly sensitive to the irradiation similarly to the nude mouse transplantation. It was rather more sensitive when compared with the two-dimensionally cultured cancer cells. When compared with the AOI cells, these cancer cells were rather resistant to cisplatin, highly sensitive to 5FU, and has a sensitivity to mitomycin similar to that of the AOI cells.

<B> Use of Lung-derived Fibroblasts as Feeder Layer 1.1 An extremely different behavior was observed when using lung-derived fibroblasts in the 1/10-fold culture medium.

Thus, no tissue exhibited any sensitivity to 5FU. To mitomycin, there was no substantial difference between the skin-derived and lung-derived fibroblasts.

2.1. An extremely different behavior was observed when using a lung-derived fibroblast in the 1-fold culture medium.

Thus, while the difference in the sensitivity of the AOI cancer tissue to cisplatin by the difference in the fibroblasts was small, the toxicity of cisplatin on the normal tissue was reduced. The 3-dimensional culture resulted in a reduced sensitivity of the AOI cancer cell tissue and the normal tissue to 5FU. The sensitivity of the 3-dimensional AOI cancer cells was increased. These results are well in agreement with the results observed when the same cancer cells were transplanted into the nude mouse.

<C> Conclusion

1. The AOI tumor transplanted actually to a nude mouse exhibits a resistance so potent that a retarded growth was observed only for several days even when treated with cisplatin at 10 mg/kg (corresponding to 10 µg/ml in a culture system) which is so toxic that the body weight of the nude mouse is reduced to about ⅔. The AOI tumor was rather more sensitive to mitomycin than to cisplatin.

2. Based on the finding described above, it was revealed that in the sensitivity comparison using the 3-dimensionally cultured normal tissue substantiated that the sensitivity may vary greatly depending on whether the fibroblasts used as a feeder layer was derived from the identical organ or not. Thus, the sensitivity can correctly be detected by preparing a feeder layer using an identical organ-derived fibroblast.

Since identical organ-derived fibroblasts can readily be available when using a clinical material, there is no problem. While an added growth factor may influence the sensitivity markedly, there is still no problem since the sensitivity was assessed rather correctly even when using a 1/10-fold culture medium.

Based on the results of the experiment described above, the use of an ectopic feeder layer (when using fibroblasts derived from the skin as a feeder layer for the lung cancer) may result in a marked variation in the reaction (sensitivity). It is also considered that also since both of the lung-derived fibroblasts (connective tissue) and the regenerated bronchial epithelial tissue was employed eventually as feeders for the cancer, the natural sensitivity (reaction) was exhibited by the lung cancer-derived cells. Such findings are also supportive of the effect of the orthotopicity.

Embodiment 4

In EMBODIMENT 2, it was revealed that the collagen gel was not essential for the regeneration in inventive organ-derived tissue regeneration, and these findings were verified also by using fibronectin which is one of the extracellular matrixes other than the collagen.

FIG. 35 shows the results for the kidney-derived cells: PrEc in the presence only of the collagen, while FIG. 36 shows the results obtained without using the collagen but using only 100 µg/ml of fibronectin. As evident from these results, the formation of a stratified structure can be accomplished also by fibronectin.

Embodiment 5

The organ-derived tissue regeneration by means of the stratified structure of the invention was validated with regard to the effect of the addition of an extracellular matrix other than the collagen gel.

Thus, similarly to EMBODIMENT 1, human skin-derived fibroblasts as a feeder layer was covered with NHDF-Ad: human skin keratinized cells to form a stratified structure with adding fibronectin and laminin to the collagen gel.

FIGS. 37(a), 37(b), 38(a) and 38(b) show the results.

As evident from these result, the addition of 2 µg/ml of fibronectin and 1 µg/ml of laminin (fibronectin:laminin=2:1) (FIG. 28) to the collagen gel gave the highest regeneration efficiency, and the ratios of 1:1 and 1:2 were the next highest in this order (FIGS. 37(a) and 37(b)), and the regeneration efficiency of the collagen gel alone (FIGS. 38(a) and 38(b)) was revealed to be poorer than the formers.

Embodiment 6

$5 \times 10^4$ cells of a human melanoma-derived SK-Mel26 cell were inoculated to a Boyden Chamber having a bed of 0.1 mg/ml MATRIGEL, and cultured together with the human keratinized epithelial cells NHDF-Ad in a stratified structure on human skin-derived fibroblasts formed by an inventive method. By observing the cell invading the MATRIGEL to emerge out on the back, the invasion test was conducted. In this procedure, the ratio of fibronectin and laminin added (F:L) to the collagen gel was varied similarly to EMBODIMENT 5. The results are shown in FIGS. 39(a) and 39(b). The invasion ability became highest also here when adding the combination of 2 ng/ml or 1 ng/ml of the former with 1 ng/ml of the latter.

Embodiment 7

The human prostate epithelium-derived PrEc cells on the 3rd day in EMBODIMENT 4 described above when altering the culture condition were shown as photographs in FIGS. 40 to 42.

The even numbers correspond to the addition of 2.5 µl of fibronectin and 2.5 µl of laminin to 500 µl of the collagen (F:L=1:1).

The odd numbers correspond to the addition of 5 µl of fibronectin and 2.5 µl of laminin to 500 µl of the collagen (F:L=2:1).

Numbers 1 and 2 employed 250 µl/well of the type 1 collagen alone.

Numbers 3 and 4 employed 200 µl/well of the type 1 collagen together with 50 µl/well of the type 2 collagen.

Numbers 5 and 6 employed 200 µl/well of the type 1 collagen together with 50 µl/well of the type 3 collagen.

Numbers 7 and 8 employed 200 µl/well of the type 1 collagen together with 50 µl/well of the type 4 collagen.

Numbers 9 and 10 employed 200 µl/well of the type I collagen together with 50 µl/well of the type 5 collagen.

Numbers 11 and 12 employed 150 µl/well of the type 1 collagen together with 25 µl/well of the type 2, 25 µl/well of the type 3, 25 µl/well of the type 4 and 25 µl/well of the type 5, thus employing 5 types in total.

It was observed that any of the samples having odd numbers generally exhibited an advanced stage of the statification, and the difference in the collagen type was not reflected in the prostatic epithelium.

Embodiment 8

Figure 43:
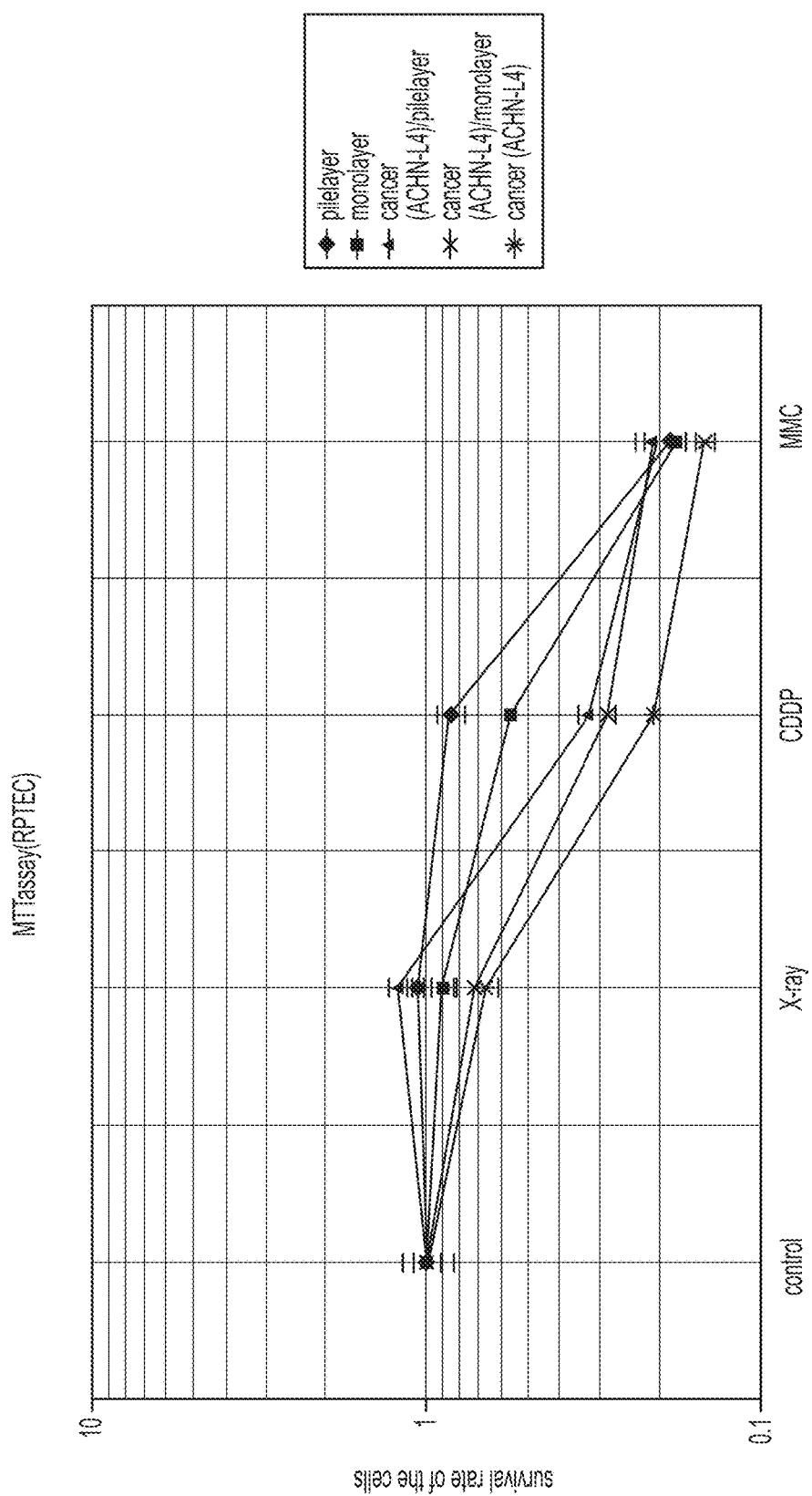
FIGS. 43 and 44 show the results of the sensitivity test using human renal cancer-derived ACHN-L4 cells for each of a human renal proximal tubular epithelial cells (RPTEC) and mesangium cells (NHMC) each regenerated in a stratified structure.
Figure 44:
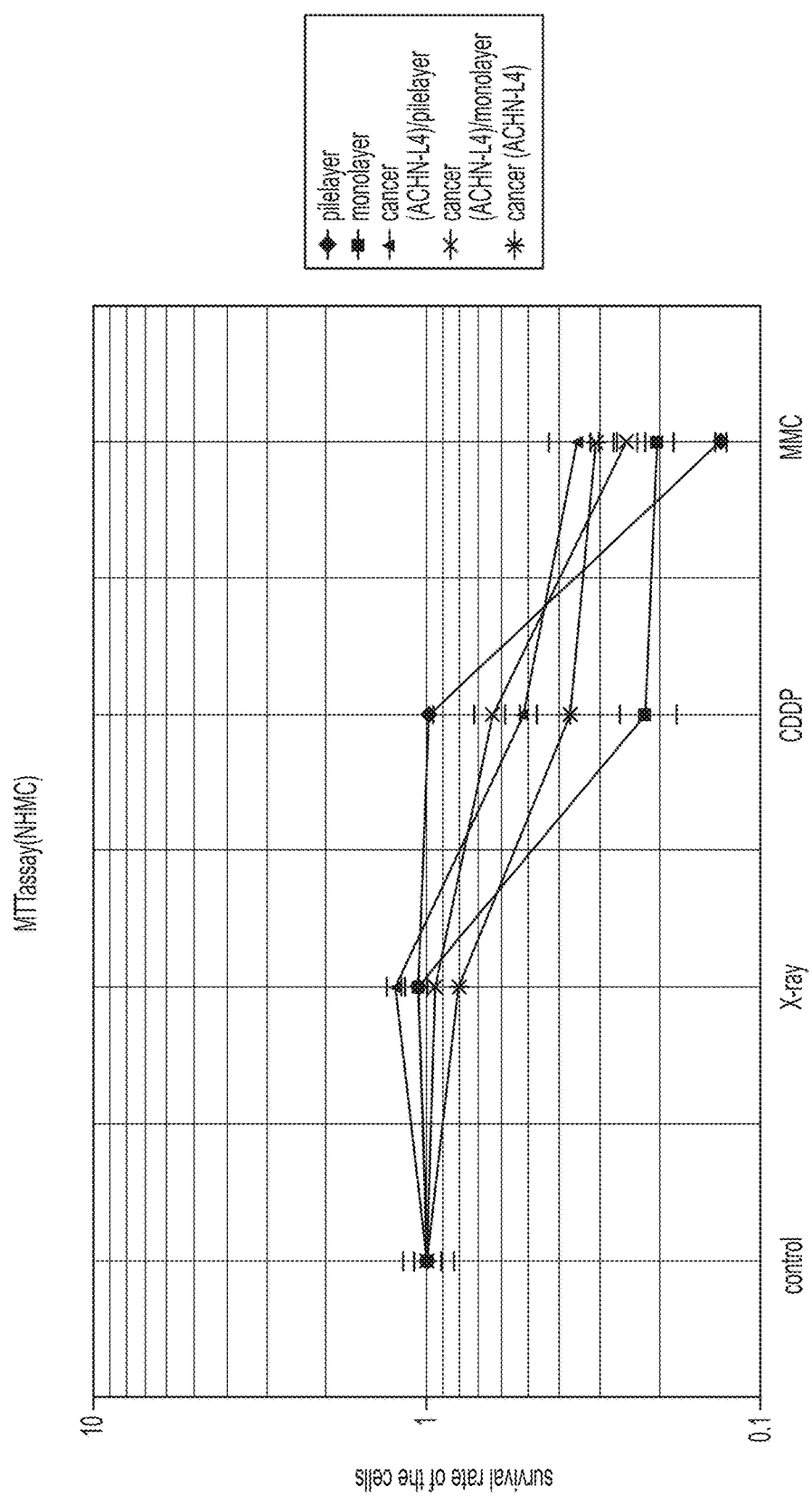

A human kidney cancer-derived ACHN-L4 was employed as cancer cells to conduct a cancer therapy sensitivity test. The results are shown in FIGS. 43 and 44. For an ACHN-L4/pilelayer, a Boyden chamber having a bed of 0.1 mg/ml of MATRIGEL on the stratified structure of each of human renal proximal tubular epithelial cells (RPTEC) and mesangium cells (NHMC) (Day 9) was employed. In the chamber, $5 \times 10^4$ cells of the ACHN-L4 were inoculated, and subjected to the irradiation after 24 hours or the drug treatment for 72 hours followed by a therapy effect evaluation such as an MTT assay. For a monolayer, a Boyden chamber having a bed of 0.1 mg/ml of MATRIGEL on the RPTEC cells or the NHMC cells were employed. In the chamber, $5 \times 10^4$ cells of the ACHN-L4 were inoculated, and subjected to the irradiation after 24 hours or the drug treatment for 72 hours followed by a therapy effect evaluation such as an MTT assay. A cancer (ACHN-L4) was subjected to the therapy sensitivity test similarly except for using no underlying feeder layer, RPTEC or NHMC.

The X-ray dose employed here was 10Gy, and both of the CDDP at 10 µg/ml and the MMC at 100 µg/ml were applied to the top and the bottom of the Boyden chamber.

The % viability was calculated from the difference in the absorbance between those at the wavelengths of 550 nm and 690 nm (X550-Y690).

Figure 45:
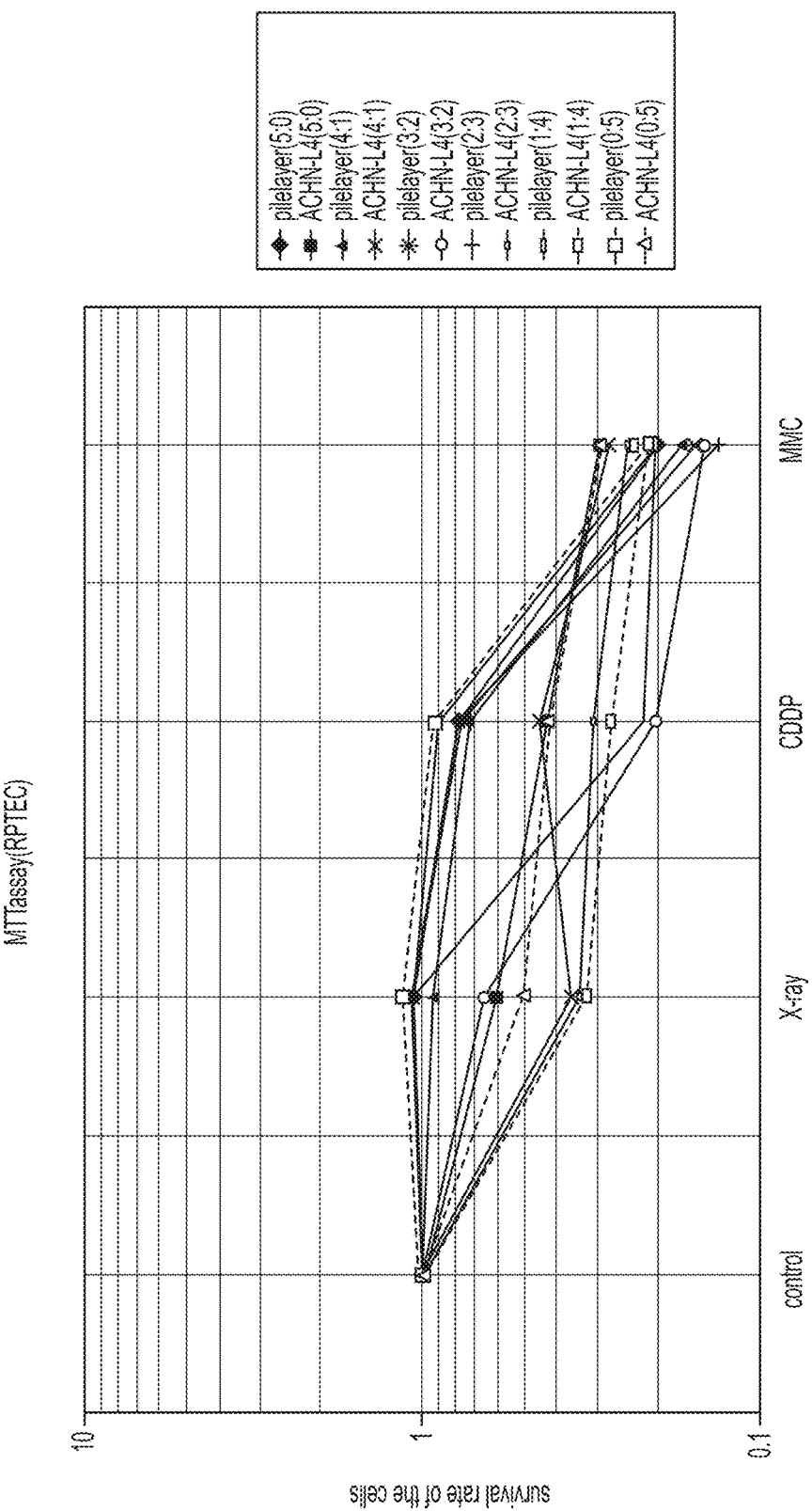
FIG. 45 shows the effect of the addition of the culture supernatant of skin keratinized cell-derived NHDF-Ad cells for the RPTEC in a stratified structure.

FIG. 45 shows the change in the sensitivity of the human renal proximal tubular epithelial cells RPTEC in a mixed culture medium prepared by adding the culture supernatant of a skin keratinized cell-derived NHDF-Ad cells (derived from heterotopic organ) in a stratified structure (After two days of culture incubation) to a fresh maintenance medium in the ratios of 5:0, 4:1, 3:2 and the like.

Figure 46C:
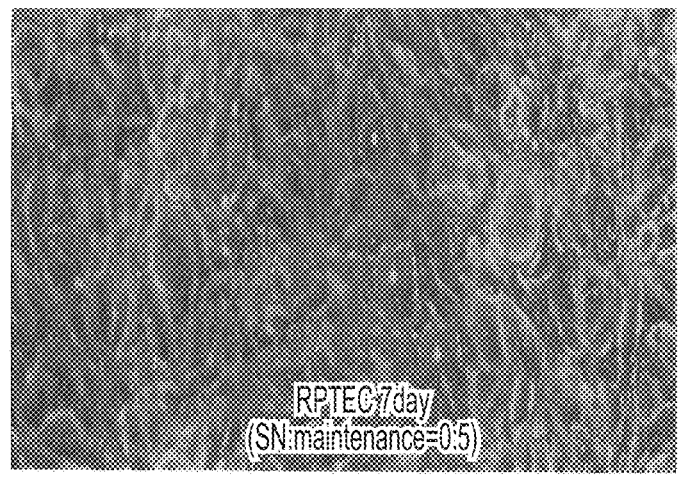

FIGS. 46(a)-46(c) are photographs showing the condition in the case described above.

In the experiments described above, it was verified that the MTT assay employing a Boyden chamber enables an easy separation between the cancer cells and the normal cells, whereby improving the quantitativity.

Also in view of the results of the MTT assay, the two-dimensional culture (monolayer) and the 3-dimensional culture (pile-layer) exhibited the sensitivity to a therapy in the presence of a normal tissue which was different substantially even when comparing with conventional cancer cells employed alone. It was also proven that the toxic profile observed in the normal tissue was different between the two-dimensional culture (monolayer) and the 3-dimensional culture (pilelayer). Also in the case of the coexistence, the cancer cell reaction varies depending on the type of the normal tissue derived from an identical human kidney.

It was also observed quantitatively that the cancer cell sensitivity was altered when the culture supernatant of a tissue in a stratified structure derived from a different organ was mixed. Thus it was proven that the circulation between the organs is of a great significance for example in a toxicity test.

INDUSTRIAL APPLICABILITY

As detailed above, the invention overcomes the limitations and the problems associated with the prior art described above, and make it possible to obtain a regenerated tissue simply and reliably by a 3-dimensional culture from a human-derived normal tissue as a base, and to provide, while utilizing the formers, a method for constructing a system for assessing the effects and the side effects of a chemical substance such as a pharmaceutical using a thus regenerated tissue as a respective organ model or a system for assessing the sensitivity and the like.

The invention claimed is:

1. An isolated regenerated tissue comprising a stratified structure of epithelial cells on an irradiated feeder layer of fibroblast and vascular endothelial cells obtained from an organ, wherein the fibroblasts, the endothelial cells and the epithelial cells are orthotopic with regard to the originating organ, wherein the organ is not skin; wherein the feeder layer is formed by irradiating the combination of the vascular endothelial cells and the fibroblast cells with 20 Gy or less X-ray or γ-ray; and wherein a ratio of the fibroblasts to the vascular endothelial cells is 10:1.

2. The isolated regenerated tissue according to claim 1, wherein the epithelial cells are selected from the group consisting of oral mucosa epithelial cells, bronchus epithelial cells, mammary gland epithelial cells, liver epithelial cells, prostate epithelial cell, and kidney epithelial cells.

3. The isolated regenerated tissue according to claim 1, wherein the feeder layer consists of a lower layer of the fibroblasts and upper layer of the endothelial cells.

4. The isolated regenerated tissue according to claim 1, wherein the epithelial cells are in a stratified structure consisting of four or more layers.

5. The isolated regenerated tissue according to claim 1, wherein the regenerated tissue is on a basal plate.

6. The isolated regenerated tissue according to claim 1, wherein the regenerated tissue contacts a culture medium or culture fluid.

7. An in vitro organ model comprising the isolated regenerated tissue according to claim 1.

* * * * *